US006777232B1

(12) United States Patent
Walke et al.

(10) Patent No.: US 6,777,232 B1
(45) Date of Patent: Aug. 17, 2004

(54) HUMAN MEMBRANE PROTEINS AND POLYNUCLEOTIDES ENCODING THE SAME

(75) Inventors: D. Wade Walke, Spring, TX (US); John Scoville, Houston, TX (US)

(73) Assignee: Lexicon Genetics Incorporated, The Woodlands, TX (US)

(*) Notice: Subject to any disclaimer, the term of this patent is extended or adjusted under 35 U.S.C. 154(b) by 25 days.

(21) Appl. No.: 09/969,532

(22) Filed: Oct. 2, 2001

Related U.S. Application Data

(60) Provisional application No. 60/237,280, filed on Oct. 2, 2000.

(51) Int. Cl.⁷ .......................... C12N 15/85; C12N 1/21; C12N 1/15; C12N 15/63; C07H 21/04

(52) U.S. Cl. ............... 435/325; 435/252.3; 435/254.11; 435/254.2; 435/320.1; 536/23.5

(58) Field of Search .......................... 536/23.1, 23.5, 536/24.3; 435/320.1, 325, 252.3, 254.11, 254.2

(56) References Cited

U.S. PATENT DOCUMENTS

| | | |
|---|---|---|
| 4,215,051 A | 7/1980 | Schroeder et al. |
| 4,376,110 A | 3/1983 | David et al. |
| 4,594,595 A | 6/1986 | Struckman |
| 4,631,211 A | 12/1986 | Houghten |
| 4,689,405 A | 8/1987 | Frank et al. |
| 4,713,326 A | 12/1987 | Dattagupta et al. |
| 4,873,191 A | 10/1989 | Wagner et al. |
| 4,946,778 A | 8/1990 | Ladner et al. |
| 5,252,743 A | 10/1993 | Barrett et al. |
| 5,272,057 A | 12/1993 | Smulson et al. |
| 5,424,186 A | 6/1995 | Fodor et al. |
| 5,445,934 A | 8/1995 | Fodor et al. |
| 5,459,127 A | 10/1995 | Felgner et al. |
| 5,556,752 A | 9/1996 | Lockhart et al. |
| 5,700,637 A | 12/1997 | Southern |
| 5,744,305 A | 4/1998 | Fodor et al. |
| 5,830,721 A | 11/1998 | Stemmer et al. |
| 5,837,458 A | 11/1998 | Minshull et al. |
| 5,869,336 A | 2/1999 | Meyer et al. |
| 5,877,397 A | 3/1999 | Lonberg et al. |
| 5,948,767 A | 9/1999 | Scheule et al. |
| 6,075,181 A | 6/2000 | Kucherlapati et al. |
| 6,110,490 A | 8/2000 | Thierry |
| 6,150,584 A | 11/2000 | Kucherlapati et al. |

OTHER PUBLICATIONS

Ji et al. G–protein–coupled receptors, J. Biol. Chem. 273:17299–17302, 1998.*
Peer Bork and Eugene V. Koonin, Predicting functions from protein sequences—where are the bottlenecks? Nature Genetics 18:313–318, 1998.*
Yan et al, Two–amino acid moleculsr switch in an epithelial morphogen that regulates binding to two distinct receptors. Science, 290:523–527, 2000.*
Adams et al. EMBL Database, Accession No. AQ311659, May 4, 1999.*
Morrison et al, 1984, "Chimeric human antibody molecules: Mouse antigen–binding domains with human constant region domains", Proc. Natl. Acad. Sci. USA 81:6851–6855.
Mulligan & Berg, 1981, "Selection for animal cells that express the *Escherichia coli* gene coding for xanthine–guanine phosphoribosyltransferase", Proc. Natl. Acad. Sci. USA 78(4):2072–2076.
Neuberger et al, 1984, "Recombinant antibodies possessing novel effector functions", Nature 312:604–608.
Nisonoff, 1991, "Idiotypes: Concepts and Applications", J. of Immunology 147:2429–2436.
O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.
Ruther et al, 1983, "Easy identification of cDNA clones", EMBO Journal 2(10):1791–1794.
Santerre et al, 1984, "Expression of prokaryotic genes for hygromycin B and G418 resistance as dominant–selection markers in mouse L cells", Gene 30:147–156.
Sarin et al., 1988, "Inhibition of acquired immunodeficiency syndrome virus by oligodeoxynucleoside methylphosphonates", Proc. Natl. Acad. Sci. USA 85:7448–7451.
Smith et al., 1983, "Molecular Engineering of the *Autographa californica* Nuclear Polyhedrosis Virus Genome: Deletion Multations within the Polyhedrin Gene", J. Virol. 46(2):584–593.
Stein et al., 1988, "Physiochemical properties of phosphorothioate oligodeoxynucleotides", Nucleic Acids Research 16(8):3209–3221.
Szybalska & Szybalski, 1962, "Genetics of Human Cell Lines, IV. DNA–Mediated Heritable Transformation of a Biochemical Trait", Proc. Natl. Acad. Sci. USA 48:2026–2034.
Takeda et al, 1985, "Construction of chimaeric processed immunoglobulin genes containing mouse variable and human constant region sequences", Nature 314:452–454.
Thompson et al, 1989, "Germ Line Transmission and Expression of a Corrected HPRT Gene Produced by Gene Targeting in Embryonic Stem Cells", Cell 56:313–321.
Van Der. Putten et al, 1985, "Efficient insertion of genes into the mouse germ line via retroviral vectors", Proc. Natl. Acad. Sci. USA 82:6148–6152.

(List continued on next page.)

*Primary Examiner*—Gary Kunz
*Assistant Examiner*—Ruixiang Li

(57) ABSTRACT

Novel human polynucleotide and polypeptide sequences are disclosed that can be used in therapeutic, diagnostic, and pharmacogenomic applications.

6 Claims, No Drawings

OTHER PUBLICATIONS

Van Heeke et al, 1989, "Expression of Human Asparagine Synthetase in *Escherichia coli*", J. Biol. Chemistry 264(10):5503–5509.

Ward et al, 1989, "Binding activities of a repertoire of single immunoglobulin variable domains secreted from *Escherichia coli*", Nature 341:544–546.

Wigler et al, 1977, "Transfer of Purified Herpes Virus Thymidine Kinase Gene to Cultured Mouse Cells", Cell 11:223–232.

Wigler et al, 1980, "Transformation of mammalian cells with an amplifiable dominant–acting gene", Proc. Natl. Acad. Sci. USA 77(6):3567–3570.

Bird et al, 1988, "Single–Chain Antigen–Binding Proteins", Science 242:423–426.

Bitter et al., 1987, "Expression and Secretion Vectors for Yeast", Methods in Enzymology 153:516–544.

Colbere–Garapin et al, 1981, "A New Dominant Hybrid Selective Marker for Higher Eukaryotic Cells", J. Mol. Biol. 150:1–14.

Gautier et al, 1987, "α–DNA IV:α anomeric and β–anomeric tetrathymidylates covalently linked to intercalating oxazolopyridocarbazole. Synthesis, physiochemical properties and poly (rA) binding", Nucleic Acids Research 15(16):6625–6641.

Gordon, 1989, "Transgenic Animals", International Review of Cytology, 115:171–229.

Greenspan et al, 1993, "Idiotypes: structure and immunogenicity", FASEB Journal 7:437–444.

Gu et al, 1994, "Deletion of a DNA Polymerase β Gene Segment in T Cells Using Cell Type–Specific Gene Targeting", Science 265:103–106.

Huse et al, 1989, "Generation of a Large Combinatorial Library of the Immunoglobulin Repertoire in Phage Lambda", Science 246:1275–1281.

Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.

Inoue et al, 1987, "Sequence–dependent hydroylsis of RNA using modified oligonucleotide splints and R Nase H", FEBS Letters 215(2):327–330.

Inoue et al, 1987, "Synthesis and hybridization studies on two complementary nona(2'–O–methyl)ribonucleotides", Nucleic Acids Research 15(15):6131–6149.

Inouye & Inouye, 1985, "Up–promoter mutations in the Ipp gene of *Escherichia coli*", Nucleic Acids Research 13(9):3101–3110.

Janknecht et al, 1991, "Rapid and efficient purification of native histidine–tagged protein expressed in recombinant vaccinia virus", PNAS 88:8972–8976.

Kohler & Milstein, 1975, "Continuous cultures of fused cells secreting antibody of predefined specificity", Nature 256:495–497.

Lakso et al, 1992, "Targeted oncogene activation by site–specific recombination in transgenic mice", Proc. Natl. Acad. Sci. USA 89:6232–6236.

Lavitrano et al, 1989, "Sperm Cells as Vectors for Introducing Foreign DNA into Eggs: Genetic Transformation of Mice", Cell 57:717–723.

Lo, 1983, "Transformation by Iontophoretic Microinjection of DNA: Multiple Integrations without Tandem Insertions", Mol. & Cell. Biology 3(10):1803–1814.

Logan et al, 1984, "Adenovirus tripartite leader sequence enhances translation of mRNAs late after infection", Proc. Natl. Acad. Sci. USA 81:3655–3659.

Lowy et al, 1980, "Isolation of Tranforming DNA: Cloning the Hamster aprt Gene", Cell 22:817–823.

\* cited by examiner

HUMAN MEMBRANE PROTEINS AND POLYNUCLEOTIDES ENCODING THE SAME

The present application claims the benefit of U.S. Provisional Application No. 60/237,280, which was filed on Oct. 2, 2000, and is herein incorporated by reference in its entirety.

1. INTRODUCTION

The present invention relates to the discovery, identification, and characterization of novel human polynucleotides encoding proteins that share sequence similarity with mammalian membrane proteins. The invention encompasses the described polynucleotides, host cell expression systems, the encoded proteins, fusion proteins, polypeptides and peptides, antibodies to the encoded proteins and peptides, and genetically engineered animals that either lack or over express the disclosed genes, antagonists and agonists of the proteins, and other compounds that modulate the expression or activity of the proteins encoded by the disclosed genes that can be used for diagnosis, drug screening, clinical trial monitoring, the treatment of diseases and disorders, and cosmetic or nutriceutical applications.

2. BACKGROUND OF THE INVENTION

In addition to providing the structural and mechanical scaffolding for cells and tissues, proteins can also serve as recognition markers, mediate signal transduction, and can mediate or facilitate the passage of materials across the lipid bilayer. As such, proteins, and particularly protein ligands and membrane receptor proteins, are good drug targets and soluble formulations thereof can directly serve as therapeutic agents.

3. SUMMARY OF THE INVENTION

The present invention relates to the discovery, identification, and characterization of nucleotides that encode novel human proteins, and the corresponding amino acid sequences of these proteins. The novel human proteins (NHPs) described for the first time herein share structural similarity with mammalian protein and peptide receptors and particularly proteins of the Unc5 family, which are putative netrin receptors.

The novel human nucleic acid sequences described herein encode alternative proteins/open reading frames (ORFs) of 577, 566, 563, 552, 911, 900, 897, 886, 346, 335, 332, 321, 680, 669, 666, and 655 amino acids in length (SEQ ID NOS: 2, 4, 6, 8, 10, 12, 14, 16, 18, 20, 22, 24, 26, 28, 30, and 32).

The invention also encompasses agonists and antagonists of the described NHPs, including small molecules, large molecules, mutant NHPs, or portions thereof, that compete with native NHP, peptides, and antibodies, as well as nucleotide sequences that can be used to inhibit the expression of the described NHPs (e.g., antisense and ribozyme molecules, and open reading frame or regulatory sequence replacement constructs) or to enhance the expression of the described NHPs (e.g., expression constructs that place the described polynucleotide under the control of a strong promoter system), and transgenic animals that express a NHP sequence, or "knock-outs" (which can be conditional) that do not express a functional NHP. Knock-out mice can be produced in several ways, one of which involves the use of mouse embryonic stem cells ("ES cells") lines that contain gene trap mutations in a murine homolog of at least one of the described NHPs. When the unique NHP sequences described in SEQ ID NOS:1–33 are "knocked-out" they provide a method of identifying phenotypic expression of the particular gene as well as a method of assigning function to previously unknown genes. In addition, animals in which the unique NHP sequences described in SEQ ID NOS:1–33 are "knocked-out" provide a unique source in which to elicit antibodies to homologous and orthologous proteins, which would have been previously viewed by the immune system as "self" and therefore would have failed to elicit significant antibody responses.

Additionally, the unique NHP sequences described in SEQ ID NOS:1–33 are useful for the identification of protein coding sequence and mapping a unique gene to a particular chromosome. These sequences identify biologically verified exon splice junctions as opposed to splice junctions that may have been bioinformatically predicted from genomic sequence alone. The sequences of the present invention are also useful as additional DNA markers for restriction fragment length polymorphism (RFLP) analysis, and in forensic biology.

Further, the present invention also relates to processes for identifying compounds that modulate, i.e., act as agonists or antagonists, of NHP expression and/or NHP activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequences of the NHP ORFs encoding the described NHP amino acid sequences. SEQ ID NO:33 describes a polynucleotide encoding a NHP ORF with regions of flanking sequence.

5. DETAILED DESCRIPTION OF THE INVENTION

The NHPs described for the first time herein are novel proteins that may be expressed in, inter alia, human cell lines, fetal brain, brain, pituitary, cerebellum, spinal cord, thymus, kidney, prostate, testis, adrenal gland, stomach, small intestine, mammary gland, esophagus, bladder, cervix, pericardium, and fetal kidney cells.

The present invention encompasses the nucleotides presented in the Sequence Listing, host cells expressing such nucleotides, the expression products of such nucleotides, and: (a) nucleotides that encode mammalian homologs of the described genes, including the specifically described NHPS, and the NHP products; (b) nucleotides that encode one or more portions of the NHPs that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal (or hydrophobic transmembrane) sequence is deleted; (d) nucleotides that encode chimeric fusion proteins containing all or a portion of a coding region of an NHP, or one of its domains (e.g., a receptor or ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing.

As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel et al., eds., 1989, Current Protocols in Molecular Biology, Vol. I, Green Publishing Associates, Inc., and John Wiley & sons, Inc., New York, at p. 2.10.3) and encodes a functionally equivalent expression product. Additionally contemplated are any nucleotide sequences that hybridize to the complement of a DNA sequence that encodes and expresses an amino acid sequence presented in the Sequence Listing under moderately stringent conditions, e.g., washing in 0.2×SSC/0.1% SDS at 42° C. (Ausubel et al., 1989, supra), yet still encodes a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

Additionally contemplated are polynucleotides encoding NHP ORFS, or their functional equivalents, encoded by polynucleotide sequences that are about 99, 95, 90, or about 85 percent similar or identical to corresponding regions of the nucleotide sequences of the Sequence Listing (as measured by BLAST sequence comparison analysis using, for example, the GCG sequence analysis package using standard default settings).

The invention also includes nucleic acid molecules, preferably DNA molecules, that hybridize to, and are therefore the complements of, the described NHP gene nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS: 1–33 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–33, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1–33 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–33.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1–33 provides detailed information about transcriptional changes involved in a specific pathway, potentially leading to the identification of novel components or gene functions that manifest themselves as novel phenotypes.

Probes consisting of sequences first disclosed in SEQ ID NOS:1–33 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–33 can be utilized in microarrays or other assay formats, to screen collections of genetic material from patients who have a particular medical condition. These investigations can also be carried out using the sequences first disclosed in SEQ ID NOS:1–33 in silico and by comparing previously collected genetic databases and the disclosed sequences using computer software known to those in the art.

Thus the sequences first disclosed in SEQ ID NOS:1–33 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–33. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relative to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP gene nucleic acid sequences). With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety that is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g., by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, supra.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

For example, the present sequences can be used in restriction fragment length polymorphism (RFLP) analysis to identify specific individuals. In this technique, an individuals genomic DNA is digested with one or more restriction enzymes, and probed on a Southern blot to yield unique bands for identification (as generally described in U.S. Pat. No. 5,272,057, incorporated herein by reference). In addition, the sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). Actual base sequence information can be used for identification as an accurate alternative to patterns formed by restriction enzyme generated fragments.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from human or non-human cell lines or tissue known or suspected to express an allele of a NHP gene. The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP sequence can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal sequence. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, osteoporosis, obesity, high blood pressure, connective tissue disorders, infertility, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue can be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor.)

Additionally, screening can be accomplished by screening with labeled NHP fusion proteins, such as, for example, alkaline phosphatase-NHP or NHP-alkaline phosphatase fusion proteins. In cases where a NHP mutation results in an expression product with altered function (e.g., as a result of a missense or a frameshift mutation), polyclonal antibodies to NHP are likely to cross-react with a corresponding mutant NHP expression product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculovirus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP sequence under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of a NHP, as well as compounds or nucleotide constructs that inhibit expression of a NHP sequence (transcription factor inhibitors, antisense and ribozyme molecules, or open reading frame sequence or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body. The use of engineered host cells and/or animals may offer an advantage in that such systems allow not only for the identification of compounds that bind to the endogenous receptor for an NHP, but can also identify compounds that trigger NHP-mediated activities or pathways.

Finally, the NHP products can be used as therapeutics. For example, soluble derivatives such as NHP peptides/domains corresponding to NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP receptor. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences and the corresponding deduced amino acid sequences of the described NHPs are presented in the Sequence Listing. The NHP nucleotides were obtained from clustered genomic sequence (the described NHPs are apparently encoded on human chromosome 8, see GEN-BANK accession no. AC012215), ESTs, and cDNAs from testis, prostate, adrenal gland, kidney, and pituitary mRNAs (Edge Biosystems, Gaithersburg, Md.).

Several polymorphism were identified during the sequencing of the NHPs, including a G/C polymorphism at position 776 of SEQ ID NOS:1, 3, 5, 7, 9, 11, 13 and 15 (which can result in a ser or thr at amino acid (aa) position 259 of, for example, SEQ ID NOS:2, 4, 6, 8, 10, 12, 14 and 16, respectively), a T/C polymorphism at position 788 of SEQ ID NOS:1, 3, 5, 7, 9, 11, 13 and 15 (which can result in a val or ala at aa position 263 of, for example, SEQ ID NOS:2, 4, 6, 8, 10, 12, 14 and 16, respectively), a G/C polymorphism at position 83 of SEQ ID NOS:17, 19, 21, 23, 25, 27, 29 and 31 (which can result in a ser or thr at aa position 28 of, for example, SEQ ID NOS:18, 20, 22, 24, 26, 28, 30 and 32, respectively), a T/C polymorphism at position 95 of SEQ ID NOS:17, 19, 21, 23, 25, 27, 29 and 31 (which can result in a val or ala at aa position 32 of, for example, SEQ ID NOS:18, 20, 22, 24, 26, 28, 30 and 32, respectively), a C/T polymorphism at position 1276 of SEQ ID NOS:1 and 9 (which can result in a leu or phe at aa position 426 of, for example, SEQ ID NOS:2 and 10, respectively), a C/T polymorphism at position 1243 of SEQ ID NOS:3 and 11 (which can result in a leu or phe at aa position 415 of, for example, SEQ ID NOS:4 and 12, respectively), a C/T polymorphism at position 1234 of SEQ ID NOS:5 and 13 (which can result in a leu or phe at aa position 412 of, for example, SEQ ID NOS:6 and 14, respectively), a C/T polymorphism at position 1201 of SEQ ID NOS:7 and 15 (which can result in a leu or phe at aa position 401 of, for example, SEQ ID NOS:8 and 16, respectively), a C/T polymorphism at position 583 of SEQ ID NOS:17 and 25 (which can result in a leu or phe at aa position 195 of, for example, SEQ ID NOS:18 and 26, respectively), a C/T polymorphism at position 550 of SEQ ID NOS:19 and 27 (which can result in a leu or phe at aa position 184 of, for example, SEQ ID NOS:20 and 28, respectively), a C/T polymorphism at position 541 of SEQ ID NOS:21 and 29 (which can result in a leu or phe at aa position 181 of, for example, SEQ ID NOS:22 and 30, respectively), and a C/T polymorphism at position 508 of SEQ ID NOS:23 and 31 (which can result in a leu or phe at aa position 170 of, for example, SEQ ID NOS:24 and 32, respectively). The present invention contemplates sequences comprising any of the above polymorphisms, as well as any and all combinations and permutations of the above.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721 and 5,837,458, which are herein incorporated by reference in their entirety.

NHP gene products can also be expressed in transgenic animals. Animals of any species, including, but not limited to, worms, mice, rats, rabbits, guinea pigs, pigs, micro-pigs, birds, goats, and non-human primates, e.g., baboons, monkeys, and chimpanzees may be used to generate NHP transgenic animals.

Any technique known in the art may be used to introduce a NHP transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the NHP transgene in all their cells, as well as animals that carry the transgene in some, but not all their cells, i.e., mosaic animals or somatic cell transgenic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al., 1992, Proc. Natl. Acad. Sci. USA 89:6232–6236. The regulatory sequences required for such a cell-type specific activation will depend upon the particular cell type of interest, and will be apparent to those of skill in the art.

When it is desired that a NHP transgene be integrated into the chromosomal site of the endogenous NHP gene, gene targeting is preferred. Briefly, when such a technique is to be utilized, vectors containing some nucleotide sequences homologous to the endogenous NHP gene are designed for the purpose of integrating, via homologous recombination with chromosomal sequences, into and disrupting the function of the nucleotide sequence of the endogenous NHP gene (i.e., "knockout" animals).

The transgene can also be selectively introduced into a particular cell type, thus inactivating the endogenous NHP gene in only that cell type, by following, for example, the teaching of Gu et al., 1994, Science, 265:103–106. The regulatory sequences required for such a cell-type specific inactivation will depend upon the particular cell type of interest, and will be apparent to those of skill in the art.

Once transgenic animals have been generated, the expression of the recombinant NHP gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include but are not limited to Northern blot analysis of tissue samples obtained from the animal, in situ hybridization analysis, and RT-PCR. Samples of NHP gene-expressing tissue, may also be evaluated immunocytochemically using antibodies specific for the NHP transgene product.

5.2 NHPS and NHP Polypeptides

NHPs, NHP polypeptides, NHP peptide fragments, mutated, truncated, or deleted forms of the NHPs, and/or NHP fusion proteins can be prepared for a variety of uses. These uses include, but are not limited to, the generation of antibodies, as reagents in diagnostic assays, for the identification of other cellular gene products related to a NHP, as reagents in assays for screening for compounds that can be used as pharmaceutical reagents useful in the therapeutic treatment of mental, biological, or medical disorders and disease. Given the similarity information and expression data, the described NHPs can be targeted (by drugs, oligos, antibodies, etc.,) in order to treat disease, or to therapeutically augment the efficacy of, for example, chemotherapeutic agents used in the treatment of cancer, arthritis, or as antiviral agents.

The Sequence Listing discloses the amino acid sequences encoded by the described NHP sequences. The NHPs display initiator methionines in DNA sequence contexts consistent with translation initiation sites, and a hydrophobic region near the N-terminus that may serve as a signal sequence, which indicates that the described NHPs can be secreted, membrane-associated, or cytoplasmic.

The NHP amino acid sequences of the invention include the amino acid sequence presented in the Sequence Listing as well as analogues and derivatives thereof. Further, corresponding NHP homologues from other species are encompassed by the invention. In fact, any NHP protein encoded by the NHP nucleotide sequences described above are within the scope of the invention as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but that result in a silent change, thus producing a functionally equivalent expression product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where, as in the present instance, the NHP peptide or polypeptide is thought to be membrane protein, the hydrophobic regions of the protein can be excised and the resulting soluble peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target expression product can be released from the GST moiety.

In an insect system, *Autographa californica* nuclear polyhedrosis virus (AcNPV) is used as a vector to express foreign polynucleotide sequences. The virus grows in *Spodoptera frugiperda* cells. A NHP coding sequence can be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted sequence is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter et al., 1987, Methods in Enzymol. 153:516–544).

In addition, a host cell strain may be chosen that modulates the expression of the inserted sequences, or modifies and processes the expression product in the specific fashion desired. Such modifications (e.g., glycosylation) and processing (e.g., cleavage) of protein products may be important for the function of the protein. Different host cells have characteristic and specific mechanisms for the post-translational processing and modification of proteins and expression products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the expression product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines that stably express the NHP sequences described above can be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci, which in turn can be cloned and expanded into cell lines. This method may advantageously be used to engineer cell lines that express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes, which can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the sequence of interest is subcloned into a vaccinia recombination plasmid such that the sequencers open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

Also encompassed by the present invention are fusion proteins that direct the NHP to a target organ and/or facilitate transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome or lipid complex based delivery systems. Such technologies are described in "Liposomes:A Practical Approach", New, R.R.C., ed., Oxford University Press, New York and in U.S. Pat. Nos. 4,594,595, 5,459,127, 5,948,767 and 6,110,490 and their respective disclosures, which are herein incorporated by reference in their entirety. Additionally embodied are novel protein constructs engineered in such a way that they facilitate transport of the NHP to the target site or desired organ, where they cross the cell membrane and/or the nucleus where the NHP can exert its functional activity. This goal may be achieved by coupling of the NHP to a cytokine or other ligand that provides targeting specificity, and/or to a protein transducing domain (see generally U.S. applications Ser. Nos. 60/111, 701 and 60/056,713, both of which are herein incorporated by reference, for examples of such transducing sequences) to facilitate passage across cellular membranes and can optionally be engineered to include nuclear localization.

5.3 Antibodies to NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP expression product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with a NHP, an NHP peptide (e.g., one corresponding to a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, chitosan, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diphtheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique that provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures, which are herein incorporated by reference in their entirety. Also encompassed by the present invention is the use of fully humanized monoclonal antibodies as described in U.S. Pat. No. 6,150, 584 and respective disclosures, which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHP expression products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include, but are not limited to: the $F(ab')_2$ fragments, which can be produced by pepsin digestion of the antibody molecule and the Fab fragments, which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies that bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or Fab fragments of such anti-idiotypes can be used in therapeutic regimens involving a NHP mediated pathway.

Additionally given the high degree of relatedness of mammalian NHPs, the presently described knock-out mice (having never seen NHP, and thus never been tolerized to NHP) have a unique utility, as they can be advantageously applied to the generation of antibodies against the disclosed mammalian NHP (i.e., NHP will be immunogenic in NHP knock-out animals).

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated nucleic acid molecule comprising the nucleotide sequence of SEQ ID NO: 9.

2. An isolated nucleic acid molecule comprising a nucleotide sequence that:
   (a) encodes the amino acid sequence shown in SEQ ID NO:10; and
   (b) hybridizes to the nucleotide sequence of SEQ ID NO:9 or the complement thereof under highly stringent conditions of 0.5 M NaHPO$_4$, 7% sodium dodecyl sulfate (SDS) and 1 mM EDTA at 65° C. and washing in 0.1×SSC/0.1% SDS at 68° C.

3. An isolated nucleic acid molecule comprising a nucleotide sequence encoding the amino acid sequence shown in SEQ ID NO:10.

4. A recombinant expression vector comprising the isolated nucleic acid molecule of claim 1.

5. The recombinant expression vector of claim 4, wherein the isolated nucleic acid molecule encodes the amino acid sequence shown in SEQ ID NO: 10.

6. A host cell comprising the recombinant expression vector of claim 4.

* * * * *

SEQUENCE LISTING

<160> NUMBER OF SEQ ID NOS: 33

<210> SEQ ID NO 1
<211> LENGTH: 1734
<212> TYPE: DNA
<213> ORGANISM: homo sapiens

<400> SEQUENCE: 1

```
atggggagag cggcggccac cgcaggcggc ggcggagggg cgcgccgctg gctcccgtgg      60
ctggggctgt gcttctgggc ggcagggacc gcggctgccc gaggaactga caatggcgaa     120
gcccttcccg aatccatccc atcagctcct gggacactgc ctcatttcat agaggagcca     180
gatgatgctt atattatcaa gagcaaccct attgcactca ggtgcaaagc gaggccagcc     240
atgcagatat tcttcaaatg caacggcgag tgggtccatc agaacgagca cgtctctgaa     300
gagactctgg acgagagctc aggtttgaag gtccgcgaag tgttcatcaa tgttactagg     360
caacaggtgg aggacttcca tgggcccgag gactattggt gccagtgtgt ggcgtggagc     420
cacctgggta cctccaagag caggaaggcc tctgtgcgca tagcctattt acggaaaaac     480
tttgaacaag acccacaagg aagggaagtt cccattgaag gcatgattgt actgcactgc     540
cgcccaccag agggagtccc tgctgccgag gtggaatggc tgaaaaatga agagcccatt     600
gactctgaac aagacgagaa cattgacacc agggctgacc ataacctgat catcaggcag     660
gcacggctct cggactcagg aaattacacc tgcatggcag ccaacatcgt ggctaagagg     720
agaagcctgt cggccactgt tgtggtctac gtggatggga gctgggaagt gtggagcgaa     780
tggtccgtct gcagtccaga gtgtgaacat ttgcggatcc gggagtgcac agcaccaccc     840
ccgagaaatg ggggcaaatt ctgtgaaggt ctaagccagg aatctgaaaa ctgcacagat     900
ggtctttgca tcctagataa aaaacctctt catgaaataa aaccccaaag cattgagaat     960
gccagcgaca ttgctttgta ctcgggcttg ggtgctgccg tcgtggccgt tgcagtcctg    1020
gtcattggtg tcacccttta cagacggagc cagagtgact atggcgtgga cgtcattgac    1080
tcttctgcat tgacaggtgg cttccagacc ttcaacttca aaacagtccg tcaagccaag    1140
aatatcatgg aactaatgat acaagaaaaa tcctttggta actccctgct cctgaattct    1200
gccatgcagc cagatctgac agtgagccgg acatacagcg gacccatctg tctgcaggac    1260
cctctggaca aggagctcat gacagagtcc tcactcttta accctttgtc ggacatcaaa    1320
gtgaaagtcc agagctcgtt catggtttcc ctgggagtgt ctgagagagc tgagtaccac    1380
ggcaagaatc attccaggac ttttccccat ggaaacaacc acagctttag tacaatgcat    1440
cccagaaata aaatgcccta catccaaaat ctgtcatcac tccccacaag gacagaactg    1500
aggacaactg gtgtctttgg ccatttaggg gggcgcttag taatgccaaa tacagggtg     1560
```

-continued

```
agcttactca taccacacgg tgccatccca gaggagaatt cttgggagat ttatatgtcc      1620
atcaaccaag gtgaacccag tgaaaatcca gcaaacaaag gatcaaatag cttgttgaag     1680
aacacatatg ccattggggg aaaaataagc agacatctgg gttcttctcg ctga           1734
```

<210> SEQ ID NO 2
<211> LENGTH: 577
<212> TYPE: PRT
<213> ORGANISM: homo sapiens

<400> SEQUENCE: 2

```
Met Gly Arg Ala Ala Thr Ala Gly Gly Gly Gly Ala Arg Arg
  1               5                  10                  15

Trp Leu Pro Trp Leu Gly Leu Cys Phe Trp Ala Ala Gly Thr Ala Ala
                 20                  25                  30

Ala Arg Gly Thr Asp Asn Gly Glu Ala Leu Pro Glu Ser Ile Pro Ser
             35                  40                  45

Ala Pro Gly Thr Leu Pro His Phe Ile Glu Glu Pro Asp Asp Ala Tyr
         50                  55                  60

Ile Ile Lys Ser Asn Pro Ile Ala Leu Arg Cys Lys Ala Arg Pro Ala
 65                  70                  75                  80

Met Gln Ile Phe Phe Lys Cys Asn Gly Glu Trp Val His Gln Asn Glu
                 85                  90                  95

His Val Ser Glu Glu Thr Leu Asp Glu Ser Ser Gly Leu Lys Val Arg
            100                 105                 110

Glu Val Phe Ile Asn Val Thr Arg Gln Gln Val Glu Asp Phe His Gly
            115                 120                 125

Pro Glu Asp Tyr Trp Cys Gln Cys Val Ala Trp Ser His Leu Gly Thr
        130                 135                 140

Ser Lys Ser Arg Lys Ala Ser Val Arg Ile Ala Tyr Leu Arg Lys Asn
145                 150                 155                 160

Phe Glu Gln Asp Pro Gln Gly Arg Glu Val Pro Ile Glu Gly Met Ile
                165                 170                 175

Val Leu His Cys Arg Pro Pro Glu Gly Val Pro Ala Ala Glu Val Glu
            180                 185                 190

Trp Leu Lys Asn Glu Glu Pro Ile Asp Ser Glu Gln Asp Glu Asn Ile
        195                 200                 205

Asp Thr Arg Ala Asp His Asn Leu Ile Ile Arg Gln Ala Arg Leu Ser
    210                 215                 220

Asp Ser Gly Asn Tyr Thr Cys Met Ala Ala Asn Ile Val Ala Lys Arg
225                 230                 235                 240

Arg Ser Leu Ser Ala Thr Val Val Val Tyr Val Asp Gly Ser Trp Glu
                245                 250                 255

Val Trp Ser Glu Trp Ser Val Cys Ser Pro Glu Cys Glu His Leu Arg
            260                 265                 270

Ile Arg Glu Cys Thr Ala Pro Pro Arg Asn Gly Gly Lys Phe Cys
        275                 280                 285

Glu Gly Leu Ser Gln Glu Ser Glu Asn Cys Thr Asp Gly Leu Cys Ile
    290                 295                 300

Leu Asp Lys Lys Pro Leu His Glu Ile Lys Pro Gln Ser Ile Glu Asn
305                 310                 315                 320

Ala Ser Asp Ile Ala Leu Tyr Ser Gly Leu Gly Ala Ala Val Ala
                325                 330                 335

Val Ala Val Leu Val Ile Gly Val Thr Leu Tyr Arg Arg Ser Gln Ser
```

```
                   340              345              350
Asp Tyr Gly Val Asp Val Ile Asp Ser Ser Ala Leu Thr Gly Gly Phe
                355              360              365
Gln Thr Phe Asn Phe Lys Thr Val Arg Gln Ala Lys Asn Ile Met Glu
            370              375              380
Leu Met Ile Gln Glu Lys Ser Phe Gly Asn Ser Leu Leu Leu Asn Ser
385              390              395              400
Ala Met Gln Pro Asp Leu Thr Val Ser Arg Thr Tyr Ser Gly Pro Ile
                405              410              415
Cys Leu Gln Asp Pro Leu Asp Lys Glu Leu Met Thr Glu Ser Ser Leu
            420              425              430
Phe Asn Pro Leu Ser Asp Ile Lys Val Lys Val Gln Ser Ser Phe Met
        435              440              445
Val Ser Leu Gly Val Ser Glu Arg Ala Glu Tyr His Gly Lys Asn His
    450              455              460
Ser Arg Thr Phe Pro His Gly Asn Asn His Ser Phe Ser Thr Met His
465              470              475              480
Pro Arg Asn Lys Met Pro Tyr Ile Gln Asn Leu Ser Ser Leu Pro Thr
                485              490              495
Arg Thr Glu Leu Arg Thr Thr Gly Val Phe Gly His Leu Gly Gly Arg
            500              505              510
Leu Val Met Pro Asn Thr Gly Val Ser Leu Leu Ile Pro His Gly Ala
        515              520              525
Ile Pro Glu Glu Asn Ser Trp Glu Ile Tyr Met Ser Ile Asn Gln Gly
    530              535              540
Glu Pro Ser Glu Asn Pro Ala Asn Lys Gly Ser Asn Ser Leu Leu Lys
545              550              555              560
Asn Thr Tyr Ala Ile Gly Gly Lys Ile Ser Arg His Leu Gly Ser Ser
                565              570              575
Arg

<210> SEQ ID NO 3
<211> LENGTH: 1701
<212> TYPE: DNA
<213> ORGANISM: homo sapiens

<400> SEQUENCE: 3
atggggagag cggcggccac cgcaggcggc ggcggagggg cgcgccgctg gctcccgtgg      60
ctggggctgt gcttctgggc ggcagggacc gcggctgccc gaggaactga caatggcgaa     120
gcccttcccg aatccatccc atcagctcct gggacactgc ctcatttcat agaggagcca     180
gatgatgctt atattatcaa gagcaaccct attgcactca ggtgcaaagc gaggccagcc     240
atgcagatat tcttcaaatg caacggcgag tgggtccatc agaacgagca cgtctctgaa     300
gagactctgg acgagagctc aggtttgaag gtccgcgaag tgttcatcaa tgttactagg     360
caacaggtgg aggacttcca tgggcccgag gactattggt gccagtgtgt ggcgtggagc     420
cacctgggta cctccaagag caggaaggcc tctgtgcgca tagcctattt acggaaaaac     480
tttgaacaag acccacaagg aagggaagtt cccattgaag catgattgt actgcactgc     540
cgccaccag gggagtccc tgctgccgag gtggaatggc tgaaaaatga gagcccatt     600
gactctgaac aagacgagaa cattgacacc agggctgacc ataacctgat catcaggcag     660
gcacggctct cggactcagg aaattacacc tgcatggcag ccaacatcgt ggctaagagg     720
agaagcctgt cggccactgt tgtggtctac gtggatggga gctgggaagt gtggagcgaa     780
```

-continued

```
tggtccgtct gcagtccaga gtgtgaacat ttgcggatcc gggagtgcac agcaccaccc    840
ccgagaaatg ggggcaaatt ctgtgaaggt ctaagccagg aatctgaaaa ctgcacagat    900
ggtctttgca tcctaggcat tgagaatgcc agcgacattg ctttgtactc gggcttgggt    960
gctgccgtcg tggccgttgc agtcctggtc attggtgtca cccttacag acggagccag    1020 agtgactatg cgctggacgt cattgactct tctgcattga caggtggctt ccagaccttc    1080
aacttcaaaa cagtccgtca agccaagaat atcatggaac taatgataca agaaaaatcc    1140
tttggtaact ccctgctcct gaattctgcc atgcagccag atctgacagt gagccggaca    1200
tacagcggac ccatctgtct gcaggaccct ctggacaagg agctcatgac agagtcctca    1260
ctctttaacc ctttgtcgga catcaaagtg aaagtccaga gctcgttcat ggtttccctg    1320
ggagtgtctg agagagctga gtaccacggc aagaatcatt ccaggacttt tccccatgga    1380
aacaaccaca gctttagtac aatgcatccc agaaataaaa tgccctacat ccaaaatctg    1440
tcatcactcc ccacaaggac agaactgagg acaactggtg tctttggcca tttagggggg    1500
cgcttagtaa tgccaaatac aggggtgagc ttactcatac cacacggtgc catcccagag    1560
gagaattctt gggagattta tgtccatc aaccaaggtg aacccagtga aaatccagca    1620
aacaaaggat caaatagctt gttgaagaac acatatgcca ttgggggaaa aataagcaga    1680
catctgggtt cttctcgctg a                                             1701
```

<210> SEQ ID NO 4
<211> LENGTH: 566
<212> TYPE: PRT
<213> ORGANISM: homo sapiens

<400> SEQUENCE: 4

```
Met Gly Arg Ala Ala Thr Ala Gly Gly Gly Gly Ala Arg Arg
 1               5                  10                  15

Trp Leu Pro Trp Leu Gly Leu Cys Phe Trp Ala Ala Gly Thr Ala Ala
                20                  25                  30

Ala Arg Gly Thr Asp Asn Gly Glu Ala Leu Pro Glu Ser Ile Pro Ser
            35                  40                  45

Ala Pro Gly Thr Leu Pro His Phe Ile Glu Glu Pro Asp Asp Ala Tyr
        50                  55                  60

Ile Ile Lys Ser Asn Pro Ile Ala Leu Arg Cys Lys Ala Arg Pro Ala
65                  70                  75                  80

Met Gln Ile Phe Phe Lys Cys Asn Gly Glu Trp Val His Gln Asn Glu
                85                  90                  95

His Val Ser Glu Glu Thr Leu Asp Glu Ser Ser Gly Leu Lys Val Arg
            100                 105                 110

Glu Val Phe Ile Asn Val Thr Arg Gln Gln Val Glu Asp Phe His Gly
        115                 120                 125

Pro Glu Asp Tyr Trp Cys Gln Cys Val Ala Trp Ser His Leu Gly Thr
    130                 135                 140

Ser Lys Ser Arg Lys Ala Ser Val Arg Ile Ala Tyr Leu Arg Lys Asn
145                 150                 155                 160

Phe Glu Gln Asp Pro Gln Gly Arg Glu Val Pro Ile Glu Gly Met Ile
                165                 170                 175

Val Leu His Cys Arg Pro Pro Glu Gly Val Pro Ala Ala Glu Val Glu
            180                 185                 190

Trp Leu Lys Asn Glu Glu Pro Ile Asp Ser Gln Asp Glu Asn Ile
        195                 200                 205
```

```
Asp Thr Arg Ala Asp His Asn Leu Ile Ile Arg Gln Ala Arg Leu Ser
    210                 215                 220

Asp Ser Gly Asn Tyr Thr Cys Met Ala Ala Asn Ile Val Ala Lys Arg
225                 230                 235                 240

Arg Ser Leu Ser Ala Thr Val Val Tyr Val Asp Gly Ser Trp Glu
                245                 250                 255

Val Trp Ser Glu Trp Ser Val Cys Ser Pro Glu Cys Glu His Leu Arg
                260                 265                 270

Ile Arg Glu Cys Thr Ala Pro Pro Arg Asn Gly Gly Lys Phe Cys
            275                 280                 285

Glu Gly Leu Ser Gln Glu Ser Glu Asn Cys Thr Asp Gly Leu Cys Ile
        290                 295                 300

Leu Gly Ile Glu Asn Ala Ser Asp Ile Ala Leu Tyr Ser Gly Leu Gly
305                 310                 315                 320

Ala Ala Val Val Ala Val Ala Val Leu Val Ile Gly Val Thr Leu Tyr
                325                 330                 335

Arg Arg Ser Gln Ser Asp Tyr Gly Val Asp Val Ile Asp Ser Ser Ala
                340                 345                 350

Leu Thr Gly Gly Phe Gln Thr Phe Asn Phe Lys Thr Val Arg Gln Ala
        355                 360                 365

Lys Asn Ile Met Glu Leu Met Ile Gln Glu Lys Ser Phe Gly Asn Ser
370                 375                 380

Leu Leu Leu Asn Ser Ala Met Gln Pro Asp Leu Thr Val Ser Arg Thr
385                 390                 395                 400

Tyr Ser Gly Pro Ile Cys Leu Gln Asp Pro Leu Asp Lys Glu Leu Met
                405                 410                 415

Thr Glu Ser Ser Leu Phe Asn Pro Leu Ser Asp Ile Lys Val Lys Val
                420                 425                 430

Gln Ser Ser Phe Met Val Ser Leu Gly Val Ser Glu Arg Ala Glu Tyr
            435                 440                 445

His Gly Lys Asn His Ser Arg Thr Phe Pro His Gly Asn Asn His Ser
    450                 455                 460

Phe Ser Thr Met His Pro Arg Asn Lys Met Pro Tyr Ile Gln Asn Leu
465                 470                 475                 480

Ser Ser Leu Pro Thr Arg Thr Glu Leu Arg Thr Thr Gly Val Phe Gly
                485                 490                 495

His Leu Gly Gly Arg Leu Val Met Pro Asn Thr Gly Val Ser Leu Leu
            500                 505                 510

Ile Pro His Gly Ala Ile Pro Glu Glu Asn Ser Trp Glu Ile Tyr Met
    515                 520                 525

Ser Ile Asn Gln Gly Glu Pro Ser Glu Asn Pro Ala Asn Lys Gly Ser
    530                 535                 540

Asn Ser Leu Leu Lys Asn Thr Tyr Ala Ile Gly Gly Lys Ile Ser Arg
545                 550                 555                 560

His Leu Gly Ser Ser Arg
                565

<210> SEQ ID NO 5
<211> LENGTH: 1692
<212> TYPE: DNA
<213> ORGANISM: homo sapiens

<400> SEQUENCE: 5
atggggagag cggcggccac cgcaggcggc ggcggagggg cgcgccgctg gctcccgtgg      60
```

-continued

| | |
|---|---|
| ctggggctgt gcttctgggc ggcagggacc gcggctgccc gaggaactga caatggcgaa | 120 |
| gcccttcccg aatccatccc atcagctcct gggacactgc ctcatttcat agaggagcca | 180 |
| gatgatgctt atattatcaa gagcaaccct attgcactca ggtgcaaagc gaggccagcc | 240 |
| atgcagatat tcttcaaatg caacggcgag tgggtccatc agaacgagca cgtctctgaa | 300 |
| gagactctgg acgagagctc aggtttgaag gtccgcgaag tgttcatcaa tgttactagg | 360 |
| caacaggtgg aggacttcca tgggcccgag gactattggt gccagtgtgt ggcgtggagc | 420 |
| cacctgggta cctccaagag caggaaggcc tctgtgcgca tagcctattt acggaaaaac | 480 |
| tttgaacaag acccacaagg aagggaagtt cccattgaag gcatgattgt actgcactgc | 540 |
| cgccccaccag agggagtccc tgctgccgag gtggaatggc tgaaaaatga agagcccatt | 600 |
| gactctgaac aagacgagaa cattgacacc agggctgacc ataacctgat catcaggcag | 660 |
| gcacggctct cggactcagg aaattacacc tgcatggcag ccaacatcgt ggctaagagg | 720 |
| agaagcctgt cggccactgt tgtggtctac gtggatggga gctgggaagt gtggagcgaa | 780 |
| tggtccgtct gcagtccaga gtgtgaacat ttgcggatcc gggagtgcac agcaccaccc | 840 |
| ccgagaaatg ggggcaaatt ctgtgaaggt ctaagccagg aatctgaaaa ctgcacagat | 900 |
| ggtctttgca tcctagataa aaaacctctt catgaaataa accccaaag cattgagaat | 960 |
| gccagcgaca ttgctttgta ctcgggcttg ggtgctgccg tcgtggccgt tgcagtcctg | 1020 |
| gtcattggtg tcacccttta cagacggagc cagagtgact atggcgtgga cgtcattgac | 1080 |
| tcttctgcat tgacaggtgg cttccagacc ttcaacttca aaacagtccg tcaaggtaac | 1140 |
| tccctgctcc tgaattctgc catgcagcca gatctgacag tgagccggac atacagcgga | 1200 |
| cccatctgtc tgcaggaccc tctggacaag gagctcatga cagagtcctc actctttaac | 1260 |
| cctttgtcgg acatcaaagt gaaagtccag agctcgttca tggtttccct gggagtgtct | 1320 |
| gagagagctg agtaccacgg caagaatcat tccaggactt tcccccatgg aaacaaccac | 1380 |
| agctttagta caatgcatcc cagaaataaa atgccctaca tccaaaatct gtcatcactc | 1440 |
| cccacaagga cagaactgag gacaactggt gtctttggcc atttaggggg gcgcttagta | 1500 |
| atgccaaata caggggtgag cttactcata ccacacggtg ccatcccaga ggagaattct | 1560 |
| tgggagattt atatgtccat caaccaaggt gaacccagtg aaaatccagc aaacaaagga | 1620 |
| tcaaatagct tgttgaagaa cacatatgcc attgggggaa aaataagcag acatctgggt | 1680 |
| tcttctcgct ga | 1692 |

<210> SEQ ID NO 6
<211> LENGTH: 563
<212> TYPE: PRT
<213> ORGANISM: homo sapiens

<400> SEQUENCE: 6

Met Gly Arg Ala Ala Ala Thr Ala Gly Gly Gly Gly Ala Arg Arg
1               5                   10                  15

Trp Leu Pro Trp Leu Gly Leu Cys Phe Trp Ala Ala Gly Thr Ala Ala
            20                  25                  30

Ala Arg Gly Thr Asp Asn Gly Glu Ala Leu Pro Glu Ser Ile Pro Ser
        35                  40                  45

Ala Pro Gly Thr Leu Pro His Phe Ile Glu Glu Pro Asp Asp Ala Tyr
    50                  55                  60

Ile Ile Lys Ser Asn Pro Ile Ala Leu Arg Cys Lys Ala Arg Pro Ala
65                  70                  75                  80

```
Met Gln Ile Phe Phe Lys Cys Asn Gly Glu Trp Val His Gln Asn Glu
                85                  90                  95

His Val Ser Glu Glu Thr Leu Asp Glu Ser Ser Gly Leu Lys Val Arg
            100                 105                 110

Glu Val Phe Ile Asn Val Thr Arg Gln Gln Val Glu Asp Phe His Gly
        115                 120                 125

Pro Glu Asp Tyr Trp Cys Gln Cys Val Ala Trp Ser His Leu Gly Thr
    130                 135                 140

Ser Lys Ser Arg Lys Ala Ser Val Arg Ile Ala Tyr Leu Arg Lys Asn
145                 150                 155                 160

Phe Glu Gln Asp Pro Gln Gly Arg Glu Val Pro Ile Glu Gly Met Ile
                165                 170                 175

Val Leu His Cys Arg Pro Pro Glu Gly Val Pro Ala Ala Glu Val Glu
            180                 185                 190

Trp Leu Lys Asn Glu Glu Pro Ile Asp Ser Glu Gln Asp Glu Asn Ile
        195                 200                 205

Asp Thr Arg Ala Asp His Asn Leu Ile Ile Arg Gln Ala Arg Leu Ser
    210                 215                 220

Asp Ser Gly Asn Tyr Thr Cys Met Ala Ala Asn Ile Val Ala Lys Arg
225                 230                 235                 240

Arg Ser Leu Ser Ala Thr Val Val Val Tyr Val Asp Gly Ser Trp Glu
                245                 250                 255

Val Trp Ser Glu Trp Ser Val Cys Ser Pro Glu Cys Glu His Leu Arg
            260                 265                 270

Ile Arg Glu Cys Thr Ala Pro Pro Arg Asn Gly Gly Lys Phe Cys
        275                 280                 285

Glu Gly Leu Ser Gln Glu Ser Glu Asn Cys Thr Asp Gly Leu Cys Ile
    290                 295                 300

Leu Asp Lys Lys Pro Leu His Glu Ile Lys Pro Gln Ser Ile Glu Asn
305                 310                 315                 320

Ala Ser Asp Ile Ala Leu Tyr Ser Gly Leu Gly Ala Ala Val Val Ala
                325                 330                 335

Val Ala Val Leu Val Ile Gly Val Thr Leu Tyr Arg Arg Ser Gln Ser
            340                 345                 350

Asp Tyr Gly Val Asp Val Ile Asp Ser Ser Ala Leu Thr Gly Gly Phe
        355                 360                 365

Gln Thr Phe Asn Phe Lys Thr Val Arg Gln Gly Asn Ser Leu Leu Leu
    370                 375                 380

Asn Ser Ala Met Gln Pro Asp Leu Thr Val Ser Arg Thr Tyr Ser Gly
385                 390                 395                 400

Pro Ile Cys Leu Gln Asp Pro Leu Asp Lys Glu Leu Met Thr Glu Ser
                405                 410                 415

Ser Leu Phe Asn Pro Leu Ser Asp Ile Lys Val Lys Val Gln Ser Ser
            420                 425                 430

Phe Met Val Ser Leu Gly Val Ser Glu Arg Ala Glu Tyr His Gly Lys
        435                 440                 445

Asn His Ser Arg Thr Phe Pro His Gly Asn Asn His Ser Phe Ser Thr
    450                 455                 460

Met His Pro Arg Asn Lys Met Pro Tyr Ile Gln Asn Leu Ser Ser Leu
465                 470                 475                 480

Pro Thr Arg Thr Glu Leu Arg Thr Thr Gly Val Phe Gly His Leu Gly
                485                 490                 495
```

-continued

```
Gly Arg Leu Val Met Pro Asn Thr Gly Val Ser Leu Ile Pro His
            500                 505                 510

Gly Ala Ile Pro Glu Glu Asn Ser Trp Glu Ile Tyr Met Ser Ile Asn
            515                 520                 525

Gln Gly Glu Pro Ser Glu Asn Pro Ala Asn Lys Gly Ser Asn Ser Leu
        530                 535                 540

Leu Lys Asn Thr Tyr Ala Ile Gly Gly Lys Ile Ser Arg His Leu Gly
545                 550                 555                 560

Ser Ser Arg
```

<210> SEQ ID NO 7
<211> LENGTH: 1659
<212> TYPE: DNA
<213> ORGANISM: homo sapiens

<400> SEQUENCE: 7

| | | | |
|---|---|---|---|
| atggggagag cggcggccac cgcaggcggc ggcggagggg cgcgccgctg gctcccgtgg | 60 |
| ctggggctgt gcttctgggc ggcagggacc gcggctgccc gaggaactga caatggcgaa | 120 |
| gcccttcccg aatccatccc atcagctcct gggacactgc tcatttcat agaggagcca | 180 |
| gatgatgctt atattatcaa gagcaaccct attgcactca ggtgcaaagc gaggccagcc | 240 |
| atgcagatat tcttcaaatg caacggcgag tgggtccatc agaacgagca cgtctctgaa | 300 |
| gagactctgg acgagagctc aggtttgaag gtccgcgaag tgttcatcaa tgttactagg | 360 |
| caacaggtgg aggacttcca tgggcccgag gactattggt gccagtgtgt ggcgtggagc | 420 |
| cacctgggta cctccaagag caggaaggcc tctgtgcgca tagcctattt acggaaaaac | 480 |
| tttgaacaag acccacaagg aagggaagtt cccattgaag catgattgt actgcactgc | 540 |
| cgcccaccag agggagtccc tgctgccgag gtggaatggc tgaaaaatga gagcccatt | 600 |
| gactctgaac aagacgagaa cattgacacc agggctgacc ataacctgat catcaggcag | 660 |
| gcacggctct cggactcagg aaattacacc tgcatggcag ccaacatcgt ggctaagagg | 720 |
| agaagcctgt cggccactgt tgtggtctac gtggatggga ctgggaagt gtggagcgaa | 780 |
| tggtccgtct gcagtccaga gtgtgaacat tgcggatcc gggagtgcac agcaccaccc | 840 |
| ccgagaaatg gggcaaatt ctgtgaaggt ctaagccagg aatctgaaaa ctgcacagat | 900 |
| ggtcttttgca tcctaggcat tgagaatgcc agcgacattg ctttgtactc gggcttgggt | 960 |
| gctgccgtcg tggccgttgc agtcctggtc attggtgtca cccttttacag acggagccag | 1020 |
| agtgactatg gcgtggacgt cattgactct tctgcattga caggtggctt ccagaccttc | 1080 |
| aacttcaaaa cagtccgtca aggtaactcc ctgctcctga attctgccat gcagccagat | 1140 |
| ctgacagtga gccggacata cagcggaccc atctgtctgc aggaccctct ggacaaggag | 1200 |
| ctcatgacag agtcctcact ctttaaccct tgtcggaca tcaaagtgaa agtccagagc | 1260 |
| tcgttcatgg tttccctggg agtgtctgag agagctgagt accacggcaa gaatcattcc | 1320 |
| aggactttc cccatggaaa caaccacagc tttagtacaa tgcatcccag aaataaaatg | 1380 |
| ccctacatcc aaaatctgtc atcactcccc acaaggacga aactgaggac aactggtgtc | 1440 |
| tttggccatt tagggggggcg cttagtaatg ccaaatacag gggtgagctt actcatacca | 1500 |
| cacggtgcca tcccagagga gaattcttgg gagatttata tgtccatcaa ccaaggtgaa | 1560 |
| cccagtgaaa atccagcaaa caaggatca aatagcttgt tgaagaacac atatgccatt | 1620 |
| ggggaaaaa taagcagaca tctggttct tctcgctga | 1659 |

-continued

```
<210> SEQ ID NO 8
<211> LENGTH: 552
<212> TYPE: PRT
<213> ORGANISM: homo sapiens

<400> SEQUENCE: 8

Met Gly Arg Ala Ala Thr Ala Gly Gly Gly Gly Ala Arg Arg
 1               5                  10                  15

Trp Leu Pro Trp Leu Gly Leu Cys Phe Trp Ala Ala Gly Thr Ala Ala
                20                  25                  30

Ala Arg Gly Thr Asp Asn Gly Glu Ala Leu Pro Glu Ser Ile Pro Ser
            35                  40                  45

Ala Pro Gly Thr Leu Pro His Phe Ile Glu Glu Pro Asp Asp Ala Tyr
        50                  55                  60

Ile Ile Lys Ser Asn Pro Ile Ala Leu Arg Cys Lys Ala Arg Pro Ala
 65                  70                  75                  80

Met Gln Ile Phe Phe Lys Cys Asn Gly Glu Trp Val His Gln Asn Glu
                85                  90                  95

His Val Ser Glu Glu Thr Leu Asp Glu Ser Ser Gly Leu Lys Val Arg
            100                 105                 110

Glu Val Phe Ile Asn Val Thr Arg Gln Gln Val Glu Asp Phe His Gly
        115                 120                 125

Pro Glu Asp Tyr Trp Cys Gln Cys Val Ala Trp Ser His Leu Gly Thr
    130                 135                 140

Ser Lys Ser Arg Lys Ala Ser Val Arg Ile Ala Tyr Leu Arg Lys Asn
145                 150                 155                 160

Phe Glu Gln Asp Pro Gln Gly Arg Glu Val Pro Ile Glu Gly Met Ile
                165                 170                 175

Val Leu His Cys Arg Pro Pro Glu Gly Val Pro Ala Ala Glu Val Glu
            180                 185                 190

Trp Leu Lys Asn Glu Glu Pro Ile Asp Ser Glu Gln Asp Glu Asn Ile
        195                 200                 205

Asp Thr Arg Ala Asp His Asn Leu Ile Ile Arg Gln Ala Arg Leu Ser
    210                 215                 220

Asp Ser Gly Asn Tyr Thr Cys Met Ala Ala Asn Ile Val Ala Lys Arg
225                 230                 235                 240

Arg Ser Leu Ser Ala Thr Val Val Val Tyr Val Asp Gly Ser Trp Glu
                245                 250                 255

Val Trp Ser Glu Trp Ser Val Cys Ser Pro Glu Cys Glu His Leu Arg
            260                 265                 270

Ile Arg Glu Cys Thr Ala Pro Pro Arg Asn Gly Gly Lys Phe Cys
        275                 280                 285

Glu Gly Leu Ser Gln Glu Ser Glu Asn Cys Thr Asp Gly Leu Cys Ile
    290                 295                 300

Leu Gly Ile Glu Asn Ala Ser Asp Ile Ala Leu Tyr Ser Gly Leu Gly
305                 310                 315                 320

Ala Ala Val Val Ala Val Ala Val Leu Val Ile Gly Val Thr Leu Tyr
                325                 330                 335

Arg Arg Ser Gln Ser Asp Tyr Gly Val Asp Val Ile Asp Ser Ser Ala
            340                 345                 350

Leu Thr Gly Gly Phe Gln Thr Phe Asn Phe Lys Thr Val Arg Gln Gly
        355                 360                 365

Asn Ser Leu Leu Leu Asn Ser Ala Met Gln Pro Asp Leu Thr Val Ser
    370                 375                 380
```

-continued

```
Arg Thr Tyr Ser Gly Pro Ile Cys Leu Gln Asp Pro Leu Asp Lys Glu
385                 390                 395                 400

Leu Met Thr Glu Ser Ser Leu Phe Asn Pro Leu Ser Asp Ile Lys Val
            405                 410                 415

Lys Val Gln Ser Ser Phe Met Val Ser Leu Gly Val Ser Glu Arg Ala
        420                 425                 430

Glu Tyr His Gly Lys Asn His Ser Arg Thr Phe Pro His Gly Asn Asn
    435                 440                 445

His Ser Phe Ser Thr Met His Pro Arg Asn Lys Met Pro Tyr Ile Gln
450                 455                 460

Asn Leu Ser Ser Leu Pro Thr Arg Thr Glu Leu Arg Thr Thr Gly Val
465                 470                 475                 480

Phe Gly His Leu Gly Gly Arg Leu Val Met Pro Asn Thr Gly Val Ser
            485                 490                 495

Leu Leu Ile Pro His Gly Ala Ile Pro Glu Glu Asn Ser Trp Glu Ile
            500                 505                 510

Tyr Met Ser Ile Asn Gln Gly Glu Pro Ser Glu Asn Pro Ala Asn Lys
        515                 520                 525

Gly Ser Asn Ser Leu Leu Lys Asn Thr Tyr Ala Ile Gly Gly Lys Ile
    530                 535                 540

Ser Arg His Leu Gly Ser Ser Arg
545                 550
```

<210> SEQ ID NO 9
<211> LENGTH: 2736
<212> TYPE: DNA
<213> ORGANISM: homo sapiens

<400> SEQUENCE: 9

| | | |
|---|---|---|
| atggggagag cggcggccac cgcaggcggc ggcggagggg cgcgccgctg gctcccgtgg | 60 |
| ctggggctgt gcttctgggc ggcagggacc gcggctgccc gaggaactga caatggcgaa | 120 |
| gcccttcccg aatccatccc atcagctcct gggacactgc ctcatttcat agaggagcca | 180 |
| gatgatgctt atattatcaa gagcaaccct attgcactca ggtgcaaagc gaggccagcc | 240 |
| atgcagatat tcttcaaatg caacggcgag tgggtccatc agaacgagca cgtctctgaa | 300 |
| gagactctgg acgagagctc aggtttgaag gtccgcgaag tgttcatcaa tgttactagg | 360 |
| caacaggtgg aggacttcca tgggcccgag gactattggt gccagtgtgt ggcgtggagc | 420 |
| cacctgggta cctccaagag caggaaggcc tctgtgcgca tagcctattt acggaaaaac | 480 |
| tttgaacaag acccacaagg aagggaagtt cccattgaag gcatgattgt actgcactgc | 540 |
| cgcccaccag agggagtccc tgctgccgag gtggaatggc tgaaaaatga agagcccatt | 600 |
| gactctgaac aagacgagaa cattgacacc agggctgacc ataacctgat catcaggcag | 660 |
| gcacggctct cggactcagg aaattacacc tgcatggcag ccaacatcgt ggctaagagg | 720 |
| agaagcctgt cggccactgt tgtggtctac gtggatggga ctgggaagt gtggagcgaa | 780 |
| tggtccgtct gcagtccaga gtgtgaacat ttgcggatcc gggagtgcac agcaccaccc | 840 |
| ccgagaaatg ggggcaaatt ctgtgaaggt ctaagccagg aatctgaaaa ctgcacagat | 900 |
| ggtctttgca tcctagataa aaaacctctt catgaaataa accccaaag cattgagaat | 960 |
| gccagcgaca ttgctttgta ctcgggcttg gtgctgccg tcgtggccgt tgcagtcctg | 1020 |
| gtcattggtg tcacccttta cagacggagc cagagtgact atggcgtgga cgtcattgac | 1080 |
| tcttctgcat tgacaggtgg cttccagacc ttcaacttca aaacagtccg tcaagccaag | 1140 |

-continued

```
aatatcatgg aactaatgat acaagaaaaa tcctttggta actccctgct cctgaattct     1200
gccatgcagc cagatctgac agtgagccgg acatacagcg acccatctg tctgcaggac      1260 cctctggaca aggagctcat gacagagtcc tcactcttta acccttttgtc ggacatcaaa   1320 gtgaaagtcc agagctcgtt catggtttcc ctgggagtgt ctgagagagc tgagtaccac     1380
ggcaagaatc attccaggac ttttcccat ggaaacaacc acagctttag tacaatgcat     1440
cccagaaata aaatgcccta catccaaaat ctgtcatcac tccccacaag gacagaactg    1500
aggacaactg gtgtctttgg ccatttaggg gggcgcttag taatgccaaa tacaggggtg    1560
agcttactca taccacacgg tgccatccca gaggagaatt cttgggagat ttatatgtcc    1620
atcaaccaag gtgaacccag cctccagtca gatggctctg aggtgctcct gagtcctgaa    1680
gtcacctgtg gtcctccaga catgatcgtc accactccct ttgcattgac catcccgcac    1740
tgtgcagatg tcagttctga gcattggaat atccatttaa agaagaggac acagcagggc    1800
aaatgggagg aagtgatgtc agtggaagat gaatctacat cctgttactg cctttggac    1860 cccttgcgt gtcatgtgct cctggacagc tttgggacct atgcgctcac tggagagcca    1920
atcacagact gtgccgtgaa gcaactgaag gtggcggttt ttggctgcat gtcctgtaac    1980
tccctggatt acaacttgag agtttactgt gtggacaata ccccttgtgc atttcaggaa    2040
gtggtttcag atgaaaggca tcaaggtgga cagctcctgg aagaaccaaa attgctgcat    2100
ttcaaaggga ataccttag tcttcagatt tctgtccttg atattccccc attcctctgg    2160
agaattaaac cattcactgc ctgccaggaa gtcccgttct cccgcgtgtg gtgcagtaac    2220
cggcagcccc tgcactgtgc cttctccctg gagcgttata cgcccactac cacccagctg    2280
tcctgcaaaa tctgcattcg gcagctcaaa ggccatgaac agatcctcca agtgcagaca    2340
tcaatcctag agagtgaacg agaaaccatc actttcttcg cacaagagga cagcactttc    2400
cctgcacaga ctggcccaa agccttcaaa attccctact ccatcagaca gcggatttgt    2460
gctacatttg ataccccaa tgccaaggc aaggactggc agatgttagc acagaaaaac     2520
agcatcaaca ggaatttatc ttatttcgct acacaaagta gcccatctgc tgtcattttg    2580
aacctgtggg aagctcgtca tcagcatgat ggtgatcttg actccctggc ctgtgccctt    2640
gaagagattg ggaggacaca cacgaaactc tcaaacattt cagaatccca gcttgatgaa    2700
gccgacttca actacagcag gcaaaatgga ctctag                              2736
```

<210> SEQ ID NO 10
<211> LENGTH: 911
<212> TYPE: PRT
<213> ORGANISM: homo sapiens

<400> SEQUENCE: 10

```
Met Gly Arg Ala Ala Thr Ala Gly Gly Gly Gly Ala Arg Arg
 1               5                  10                  15

Trp Leu Pro Trp Leu Gly Leu Cys Phe Trp Ala Ala Gly Thr Ala Ala
            20                  25                  30

Ala Arg Gly Thr Asp Asn Gly Glu Ala Leu Pro Glu Ser Ile Pro Ser
        35                  40                  45

Ala Pro Gly Thr Leu Pro His Phe Ile Glu Glu Pro Asp Asp Ala Tyr
    50                  55                  60

Ile Ile Lys Ser Asn Pro Ile Ala Leu Arg Cys Lys Ala Arg Pro Ala
65                  70                  75                  80

Met Gln Ile Phe Phe Lys Cys Asn Gly Glu Trp Val His Gln Asn Glu
                85                  90                  95
```

-continued

```
His Val Ser Glu Glu Thr Leu Asp Glu Ser Ser Gly Leu Lys Val Arg
            100                 105                 110

Glu Val Phe Ile Asn Val Thr Arg Gln Gln Val Glu Asp Phe His Gly
            115                 120                 125

Pro Glu Asp Tyr Trp Cys Gln Cys Val Ala Trp Ser His Leu Gly Thr
            130                 135                 140

Ser Lys Ser Arg Lys Ala Ser Val Arg Ile Ala Tyr Leu Arg Lys Asn
145                 150                 155                 160

Phe Glu Gln Asp Pro Gln Gly Arg Glu Val Pro Ile Glu Gly Met Ile
                165                 170                 175

Val Leu His Cys Arg Pro Pro Glu Gly Val Pro Ala Ala Glu Val Glu
            180                 185                 190

Trp Leu Lys Asn Glu Glu Pro Ile Asp Ser Glu Gln Asp Glu Asn Ile
            195                 200                 205

Asp Thr Arg Ala Asp His Asn Leu Ile Ile Arg Gln Ala Arg Leu Ser
            210                 215                 220

Asp Ser Gly Asn Tyr Thr Cys Met Ala Ala Asn Ile Val Ala Lys Arg
225                 230                 235                 240

Arg Ser Leu Ser Ala Thr Val Val Val Tyr Val Asp Gly Ser Trp Glu
                245                 250                 255

Val Trp Ser Glu Trp Ser Val Cys Ser Pro Glu Cys Glu His Leu Arg
            260                 265                 270

Ile Arg Glu Cys Thr Ala Pro Pro Arg Asn Gly Gly Lys Phe Cys
            275                 280                 285

Glu Gly Leu Ser Gln Glu Ser Glu Asn Cys Thr Asp Gly Leu Cys Ile
    290                 295                 300

Leu Asp Lys Lys Pro Leu His Glu Ile Lys Pro Gln Ser Ile Glu Asn
305                 310                 315                 320

Ala Ser Asp Ile Ala Leu Tyr Ser Gly Leu Gly Ala Ala Val Val Ala
                325                 330                 335

Val Ala Val Leu Val Ile Gly Val Thr Leu Tyr Arg Arg Ser Gln Ser
            340                 345                 350

Asp Tyr Gly Val Asp Val Ile Asp Ser Ser Ala Leu Thr Gly Gly Phe
            355                 360                 365

Gln Thr Phe Asn Phe Lys Thr Val Arg Gln Ala Lys Asn Ile Met Glu
            370                 375                 380

Leu Met Ile Gln Glu Lys Ser Phe Gly Asn Ser Leu Leu Leu Asn Ser
385                 390                 395                 400

Ala Met Gln Pro Asp Leu Thr Val Ser Arg Thr Tyr Ser Gly Pro Ile
                405                 410                 415

Cys Leu Gln Asp Pro Leu Asp Lys Glu Leu Met Thr Glu Ser Ser Leu
            420                 425                 430

Phe Asn Pro Leu Ser Asp Ile Lys Val Lys Val Gln Ser Ser Phe Met
            435                 440                 445

Val Ser Leu Gly Val Ser Glu Arg Ala Glu Tyr His Gly Lys Asn His
450                 455                 460

Ser Arg Thr Phe Pro His Gly Asn Asn His Ser Phe Ser Thr Met His
465                 470                 475                 480

Pro Arg Asn Lys Met Pro Tyr Ile Gln Asn Leu Ser Ser Leu Pro Thr
                485                 490                 495

Arg Thr Glu Leu Arg Thr Thr Gly Val Phe Gly His Leu Gly Gly Arg
            500                 505                 510
```

```
Leu Val Met Pro Asn Thr Gly Val Ser Leu Ile Pro His Gly Ala
        515                 520                 525

Ile Pro Glu Glu Asn Ser Trp Glu Ile Tyr Met Ser Ile Asn Gln Gly
        530                 535                 540

Glu Pro Ser Leu Gln Ser Asp Gly Ser Glu Val Leu Ser Pro Glu
545                 550                 555                 560

Val Thr Cys Gly Pro Pro Asp Met Ile Val Thr Thr Pro Phe Ala Leu
                565                 570                 575

Thr Ile Pro His Cys Ala Asp Val Ser Ser Glu His Trp Asn Ile His
                580                 585                 590

Leu Lys Lys Arg Thr Gln Gln Gly Lys Trp Glu Val Met Ser Val
        595                 600                 605

Glu Asp Glu Ser Thr Ser Cys Tyr Cys Leu Leu Asp Pro Phe Ala Cys
610                 615                 620

His Val Leu Leu Asp Ser Phe Gly Thr Tyr Ala Leu Thr Gly Glu Pro
625                 630                 635                 640

Ile Thr Asp Cys Ala Val Lys Gln Leu Lys Val Ala Val Phe Gly Cys
                645                 650                 655

Met Ser Cys Asn Ser Leu Asp Tyr Asn Leu Arg Val Tyr Cys Val Asp
                660                 665                 670

Asn Thr Pro Cys Ala Phe Gln Glu Val Val Ser Asp Glu Arg His Gln
                675                 680                 685

Gly Gly Gln Leu Leu Glu Glu Pro Lys Leu Leu His Phe Lys Gly Asn
        690                 695                 700

Thr Phe Ser Leu Gln Ile Ser Val Leu Asp Ile Pro Pro Phe Leu Trp
705                 710                 715                 720

Arg Ile Lys Pro Phe Thr Ala Cys Gln Glu Val Pro Phe Ser Arg Val
                725                 730                 735

Trp Cys Ser Asn Arg Gln Pro Leu His Cys Ala Phe Ser Leu Glu Arg
                740                 745                 750

Tyr Thr Pro Thr Thr Thr Gln Leu Ser Cys Lys Ile Cys Ile Arg Gln
        755                 760                 765

Leu Lys Gly His Glu Gln Ile Leu Gln Val Gln Thr Ser Ile Leu Glu
        770                 775                 780

Ser Glu Arg Glu Thr Ile Thr Phe Phe Ala Gln Glu Asp Ser Thr Phe
785                 790                 795                 800

Pro Ala Gln Thr Gly Pro Lys Ala Phe Lys Ile Pro Tyr Ser Ile Arg
                805                 810                 815

Gln Arg Ile Cys Ala Thr Phe Asp Thr Pro Asn Ala Lys Gly Lys Asp
                820                 825                 830

Trp Gln Met Leu Ala Gln Lys Asn Ser Ile Asn Arg Asn Leu Ser Tyr
        835                 840                 845

Phe Ala Thr Gln Ser Ser Pro Ser Ala Val Ile Leu Asn Leu Trp Glu
850                 855                 860

Ala Arg His Gln His Asp Gly Asp Leu Asp Ser Leu Ala Cys Ala Leu
865                 870                 875                 880

Glu Glu Ile Gly Arg Thr His Thr Lys Leu Ser Asn Ile Ser Glu Ser
                885                 890                 895

Gln Leu Asp Glu Ala Asp Phe Asn Tyr Ser Arg Gln Asn Gly Leu
                900                 905                 910
```

<210> SEQ ID NO 11
<211> LENGTH: 2703
<212> TYPE: DNA

<213> ORGANISM: homo sapiens

<400> SEQUENCE: 11

| | | | | | |
|---|---|---|---|---|---|
| atggggagag | cggcggccac | cgcaggcggc | ggcggagggg | cgcgccgctg | gctcccgtgg | 60 |
| ctggggctgt | gcttctgggc | ggcagggacc | gcggctgccc | gaggaactga | caatggcgaa | 120 |
| gcccttcccg | aatccatccc | atcagctcct | gggacactgc | ctcatttcat | agaggagcca | 180 |
| gatgatgctt | atattatcaa | gagcaaccct | attgcactca | ggtgcaaagc | gaggccagcc | 240 |
| atgcagatat | tcttcaaatg | caacggcgag | tgggtccatc | agaacgagca | cgtctctgaa | 300 |
| gagactctgg | acgagagctc | aggtttgaag | gtccgcgaag | tgttcatcaa | tgttactagg | 360 |
| caacaggtgg | aggacttcca | tgggcccgag | gactattggt | gccagtgtgt | ggcgtggagc | 420 |
| cacctgggta | cctccaagag | caggaaggcc | tctgtgcgca | tagcctattt | acggaaaaac | 480 |
| tttgaacaag | acccacaagg | aagggaagtt | cccattgaag | gcatgattgt | actgcactgc | 540 |
| cgcccaccag | agggagtccc | tgctgccgag | gtggaatggc | tgaaaaatga | agagcccatt | 600 |
| gactctgaac | aagacgagaa | cattgacacc | agggctgacc | ataacctgat | catcaggcag | 660 |
| gcacggctct | cggactcagg | aaattacacc | tgcatggcag | ccaacatcgt | ggctaagagg | 720 |
| agaagcctgt | cggccactgt | tgtggtctac | gtggatggga | gctgggaagt | gtggagcgaa | 780 |
| tggtccgtct | gcagtccaga | gtgtgaacat | ttgcggatcc | gggagtgcac | agcaccaccc | 840 |
| ccgagaaatg | ggggcaaatt | ctgtgaaggt | ctaagccagg | aatctgaaaa | ctgcacagat | 900 |
| ggtctttgca | tcctaggcat | tgagaatgcc | agcgacattg | ctttgtactc | gggcttgggt | 960 |
| gctgccgtcg | tggccgttgc | agtcctggtc | attggtgtca | ccctttacag | acggagccag | 1020 |
| agtgactatg | gcgtggacgt | cattgactct | tctgcattga | caggtggctt | ccagaccttc | 1080 |
| aacttcaaaa | cagtccgtca | agccaagaat | atcatggaac | taatgataca | agaaaaatcc | 1140 |
| tttgtaact | ccctgctcct | gaattctgcc | atgcagccag | atctgacagt | gagccggaca | 1200 |
| tacagcggac | ccatctgtct | gcaggaccct | ctggacaagg | agctcatgac | agagtcctca | 1260 |
| ctctttaacc | ctttgtcgga | catcaaagtg | aaagtccaga | gctcgttcat | ggtttccctg | 1320 |
| ggagtgtctg | agagagctga | gtaccacggc | aagaatcatt | ccaggacttt | tcccatgga | 1380 |
| aacaaccaca | gctttagtac | aatgcatccc | agaaataaaa | tgccctacat | ccaaaatctg | 1440 |
| tcatcactcc | ccacaaggac | agaactgagg | acaactggtg | tctttggcca | tttagggggg | 1500 |
| cgcttagtaa | tgccaaatac | aggggtgagc | ttactcatac | cacacggtgc | catcccagag | 1560 |
| gagaattctt | gggagattta | tatgtccatc | aaccaaggtg | aacccagcct | ccagtcagat | 1620 |
| ggctctgagg | tgctcctgag | tcctgaagtc | acctgtggtc | ctccagacat | gatcgtcacc | 1680 |
| actcccttg | cattgaccat | cccgcactgt | gcagatgtca | gttctgagca | ttggaatatc | 1740 |
| catttaaaga | agaggacaca | gcagggcaaa | tgggaggaag | tgatgtcagt | ggaagatgaa | 1800 |
| tctacatcct | gttactgcct | tttggacccc | tttgcgtgtc | atgtgctcct | ggacagcttt | 1860 |
| gggacctatg | cgctcactgg | agagccaatc | acagactgtg | ccgtgaagca | actgaaggtg | 1920 |
| gcggttttg | gctgcatgtc | ctgtaactcc | ctggattaca | acttgagagt | ttactgtgtg | 1980 |
| gacaataccc | cttgtgcatt | tcaggaagtg | gtttcagatg | aaaggcatca | aggtggacag | 2040 |
| ctcctggaag | aaccaaaatt | gctgcatttc | aaagggaata | cctttagtct | tcagatttct | 2100 |
| gtccttgata | ttccccccatt | cctctggaga | attaaaccat | tcactgcctg | ccaggaagtc | 2160 |
| ccgttctccc | gcgtgtggtg | cagtaaccgg | cagcccctgc | actgtgcctt | ctccctggag | 2220 |
| cgttatacgc | ccactaccac | ccagctgtcc | tgcaaaatct | gcattcggca | gctcaaaggc | 2280 |

-continued

```
catgaacaga tcctccaagt gcagacatca atcctagaga gtgaacgaga aaccatcact    2340
ttcttcgcac aagaggacag cactttccct gcacagactg gccccaaagc cttcaaaatt    2400
ccctactcca tcagacagcg gatttgtgct acatttgata cccccaatgc caaaggcaag    2460
gactggcaga tgttagcaca gaaaaacagc atcaacagga atttatctta tttcgctaca    2520
caaagtagcc atctgctgt cattttgaac ctgtgggaag ctcgtcatca gcatgatggt    2580
gatcttgact ccctggcctg tgcccttgaa gagattggga ggacacacac gaaactctca    2640
aacatttcag aatcccagct tgatgaagcc gacttcaact acagcaggca aaatggactc    2700
tag                                                                  2703
```

<210> SEQ ID NO 12
<211> LENGTH: 900
<212> TYPE: PRT
<213> ORGANISM: homo sapiens
<400> SEQUENCE: 12

```
Met Gly Arg Ala Ala Thr Ala Gly Gly Gly Gly Ala Arg Arg
  1               5                  10                  15

Trp Leu Pro Trp Leu Gly Leu Cys Phe Trp Ala Ala Gly Thr Ala Ala
                 20                  25                  30

Ala Arg Gly Thr Asp Asn Gly Glu Ala Leu Pro Glu Ser Ile Pro Ser
             35                  40                  45

Ala Pro Gly Thr Leu Pro His Phe Ile Glu Glu Pro Asp Asp Ala Tyr
         50                  55                  60

Ile Ile Lys Ser Asn Pro Ile Ala Leu Arg Cys Lys Ala Arg Pro Ala
 65                  70                  75                  80

Met Gln Ile Phe Phe Lys Cys Asn Gly Glu Trp Val His Gln Asn Glu
                 85                  90                  95

His Val Ser Glu Glu Thr Leu Asp Glu Ser Ser Gly Leu Lys Val Arg
                100                 105                 110

Glu Val Phe Ile Asn Val Thr Arg Gln Gln Val Glu Asp Phe His Gly
            115                 120                 125

Pro Glu Asp Tyr Trp Cys Gln Cys Val Ala Trp Ser His Leu Gly Thr
        130                 135                 140

Ser Lys Ser Arg Lys Ala Ser Val Arg Ile Ala Tyr Leu Arg Lys Asn
145                 150                 155                 160

Phe Glu Gln Asp Pro Gln Gly Arg Glu Val Pro Ile Glu Gly Met Ile
                165                 170                 175

Val Leu His Cys Arg Pro Pro Glu Gly Val Pro Ala Ala Glu Val Glu
            180                 185                 190

Trp Leu Lys Asn Glu Glu Pro Ile Asp Ser Glu Gln Asp Glu Asn Ile
        195                 200                 205

Asp Thr Arg Ala Asp His Asn Leu Ile Ile Arg Gln Ala Arg Leu Ser
    210                 215                 220

Asp Ser Gly Asn Tyr Thr Cys Met Ala Ala Asn Ile Val Ala Lys Arg
225                 230                 235                 240

Arg Ser Leu Ser Ala Thr Val Val Tyr Val Asp Gly Ser Trp Glu
                245                 250                 255

Val Trp Ser Glu Trp Ser Val Cys Ser Pro Glu Cys Glu His Leu Arg
            260                 265                 270

Ile Arg Glu Cys Thr Ala Pro Pro Pro Arg Asn Gly Gly Lys Phe Cys
        275                 280                 285
```

```
Glu Gly Leu Ser Gln Glu Ser Glu Asn Cys Thr Asp Gly Leu Cys Ile
    290                 295                 300
Leu Gly Ile Glu Asn Ala Ser Asp Ile Ala Leu Tyr Ser Gly Leu Gly
305                 310                 315                 320
Ala Ala Val Val Ala Val Ala Val Leu Val Ile Gly Val Thr Leu Tyr
                    325                 330                 335
Arg Arg Ser Gln Ser Asp Tyr Gly Val Asp Val Ile Asp Ser Ser Ala
                340                 345                 350
Leu Thr Gly Gly Phe Gln Thr Phe Asn Phe Lys Thr Val Arg Gln Ala
                355                 360                 365
Lys Asn Ile Met Glu Leu Met Ile Gln Glu Lys Ser Phe Gly Asn Ser
    370                 375                 380
Leu Leu Leu Asn Ser Ala Met Gln Pro Asp Leu Thr Val Ser Arg Thr
385                 390                 395                 400
Tyr Ser Gly Pro Ile Cys Leu Gln Asp Pro Leu Asp Lys Glu Leu Met
                405                 410                 415
Thr Glu Ser Ser Leu Phe Asn Pro Leu Ser Asp Ile Lys Val Lys Val
                420                 425                 430
Gln Ser Ser Phe Met Val Ser Leu Gly Val Ser Glu Arg Ala Glu Tyr
                435                 440                 445
His Gly Lys Asn His Ser Arg Thr Phe Pro His Gly Asn Asn His Ser
    450                 455                 460
Phe Ser Thr Met His Pro Arg Asn Lys Met Pro Tyr Ile Gln Asn Leu
465                 470                 475                 480
Ser Ser Leu Pro Thr Arg Thr Glu Leu Arg Thr Thr Gly Val Phe Gly
                485                 490                 495
His Leu Gly Gly Arg Leu Val Met Pro Asn Thr Gly Val Ser Leu Leu
                500                 505                 510
Ile Pro His Gly Ala Ile Pro Glu Glu Asn Ser Trp Glu Ile Tyr Met
    515                 520                 525
Ser Ile Asn Gln Gly Glu Pro Ser Leu Gln Ser Asp Gly Ser Glu Val
530                 535                 540
Leu Leu Ser Pro Glu Val Thr Cys Gly Pro Pro Asp Met Ile Val Thr
545                 550                 555                 560
Thr Pro Phe Ala Leu Thr Ile Pro His Cys Ala Asp Val Ser Ser Glu
                565                 570                 575
His Trp Asn Ile His Leu Lys Lys Arg Thr Gln Gln Gly Lys Trp Glu
                580                 585                 590
Glu Val Met Ser Val Glu Asp Glu Ser Thr Ser Cys Tyr Cys Leu Leu
                595                 600                 605
Asp Pro Phe Ala Cys His Val Leu Leu Asp Ser Phe Gly Thr Tyr Ala
    610                 615                 620
Leu Thr Gly Glu Pro Ile Thr Asp Cys Ala Val Lys Gln Leu Lys Val
625                 630                 635                 640
Ala Val Phe Gly Cys Met Ser Cys Asn Ser Leu Asp Tyr Asn Leu Arg
                645                 650                 655
Val Tyr Cys Val Asp Asn Thr Pro Cys Ala Phe Gln Glu Val Val Ser
                660                 665                 670
Asp Glu Arg His Gln Gly Gly Gln Leu Leu Glu Pro Lys Leu Leu
                675                 680                 685
His Phe Lys Gly Asn Thr Phe Ser Leu Gln Ile Ser Val Leu Asp Ile
    690                 695                 700
Pro Pro Phe Leu Trp Arg Ile Lys Pro Phe Thr Ala Cys Gln Glu Val
```

```
                705                 710                 715                 720
Pro Phe Ser Arg Val Trp Cys Ser Asn Arg Gln Pro Leu His Cys Ala
                    725                 730                 735
Phe Ser Leu Glu Arg Tyr Thr Pro Thr Thr Thr Gln Leu Ser Cys Lys
                740                 745                 750
Ile Cys Ile Arg Gln Leu Lys Gly His Glu Gln Ile Leu Gln Val Gln
            755                 760                 765
Thr Ser Ile Leu Glu Ser Glu Arg Glu Thr Ile Thr Phe Phe Ala Gln
        770                 775                 780
Glu Asp Ser Thr Phe Pro Ala Gln Thr Gly Pro Lys Ala Phe Lys Ile
785                 790                 795                 800
Pro Tyr Ser Ile Arg Gln Arg Ile Cys Ala Thr Phe Asp Thr Pro Asn
                805                 810                 815
Ala Lys Gly Lys Asp Trp Gln Met Leu Ala Gln Lys Asn Ser Ile Asn
                820                 825                 830
Arg Asn Leu Ser Tyr Phe Ala Thr Gln Ser Ser Pro Ser Ala Val Ile
                835                 840                 845
Leu Asn Leu Trp Glu Ala Arg His Gln His Asp Gly Asp Leu Asp Ser
        850                 855                 860
Leu Ala Cys Ala Leu Glu Glu Ile Gly Arg Thr His Thr Lys Leu Ser
865                 870                 875                 880
Asn Ile Ser Glu Ser Gln Leu Asp Glu Ala Asp Phe Asn Tyr Ser Arg
                885                 890                 895
Gln Asn Gly Leu
            900

<210> SEQ ID NO 13
<211> LENGTH: 2694
<212> TYPE: DNA
<213> ORGANISM: homo sapiens

<400> SEQUENCE: 13
atggggagag cggcggccac cgcaggcggc ggcggagggg cgcgccgctg gctcccgtgg      60
ctggggctgt gcttctgggc ggcagggacc gcggctgccc gaggaactga caatggcgaa     120
gcccttcccg aatccatccc atcagctcct gggacactgc ctcatttcat agaggagcca     180
gatgatgctt atattatcaa gagcaaccct attgcactca ggtgcaaagc gaggccagcc     240
atgcagatat tcttcaaatg caacggcgag tgggtccatc agaacgagca cgtctctgaa     300
gagactctgg acgagagctc aggtttgaag gtccgcgaag tgttcatcaa tgttactagg     360
caacaggtgg aggacttcca tgggcccgag gactattggt gccagtgtgt ggcgtggagc     420
cacctgggta cctccaagag caggaaggcc tctgtgcgca tagcctattt acggaaaaac     480
tttgaacaag acccacaagg aagggaagtt cccattgaag gcatgattgt actgcactgc     540
cgcccaccag agggagtccc tgctgccgag gtggaatggc tgaaaaatga gagcccatt     600
gactctgaac aagacgagaa cattgacacc agggctgacc ataacctgat catcaggcag     660
gcacggctct cggactcagg aaattacacc tgcatggcag ccaacatcgt ggctaagagg     720
agaagcctgt cggccactgt tgtggtctac gtggatggga ctgggaagt gtggagcgaa     780
tggtccgtct gcagtccaga gtgtgaacat ttgcggatcc gggagtgcac agcaccaccc     840
ccgagaaatg gggcaaaatt ctgtgaaggt ctaagccagg aatctgaaaa ctgcacagat     900
ggtctttgca tcctagataa aaaacctctt catgaaataa accccaaag cattgagaat     960
gccagcgaca ttgctttgta ctcgggcttg ggtgctgccg tcgtggccgt tgcagtcctg    1020
```

-continued

```
gtcattggtg tcacccttta cagacggagc cagagtgact atggcgtgga cgtcattgac    1080
tcttctgcat tgacaggtgg cttccagacc ttcaacttca aaacagtccg tcaaggtaac    1140
tccctgctcc tgaattctgc catgcagcca gatctgacag tgagccggac atacagcgga    1200
cccatctgtc tgcaggaccc tctggacaag gagctcatga cagagtcctc actctttaac    1260
cctttgtcgg acatcaaagt gaaagtccag agctcgttca tggtttccct gggagtgtct    1320
gagagagctg agtaccacgg caagaatcat tccaggactt ttccccatgg aaacaaccac    1380
agctttagta caatgcatcc cagaaataaa atgccctaca tccaaaatct gtcatcactc    1440
cccacaagga cagaactgag gacaactggt gtctttggcc atttaggggg gcgcttagta    1500
atgccaaata caggggtgag cttactcata ccacacggtg ccatcccaga ggagaattct    1560
tgggagattt atatgtccat caaccaaggt gaacccagcc tccagtcaga tggctctgag    1620
gtgctcctga gtcctgaagt cacctgtggt cctccagaca tgatcgtcac cactcccttt    1680
gcattgacca tcccgcactg tgcagatgtc agttctgagc attggaatat ccatttaaag    1740
aagaggacac agcagggcaa atgggaggaa gtgatgtcag tggaagatga atctacatcc    1800
tgttactgcc ttttggaccc ctttgcgtgt catgtgctcc tggacagctt tgggacctat    1860
gcgctcactg gagagccaat cacagactgt gccgtgaagc aactgaaggt ggcggttttt    1920
ggctgcatgt cctgtaactc cctggattac aacttgagag tttactgtgt ggacaatacc    1980
ccttgtgcat tcaggaagt ggtttcagat gaaaggcatc aaggtggaca gctcctggaa    2040
gaaccaaaat tgctgcattt caagggaat acctttagtc ttcagatttc tgtccttgat    2100
attcccccat tcctctggag aattaaacca ttcactgcct gccaggaagt cccgttctcc    2160
cgcgtgtggt gcagtaaccg gcagcccctg cactgtgcct tctccctgga gcgttatacg    2220
cccactacca cccagctgtc ctgcaaaatc tgcattcggc agctcaaagg ccatgaacag    2280
atcctccaag tgcagacatc aatcctagag agtgaacgag aaaccatcac tttcttcgca    2340
caagaggaca gcacttttccc tgcacagact ggccccaaag ccttcaaaat tccctactcc    2400
atcagacagc ggatttgtgc tacatttgat accccccaatg ccaaaggcaa ggactggcag    2460
atgttagcac agaaaaacag catcaacagg aatttatctt atttcgctac acaaagtagc    2520
ccatctgctg tcattttgaa cctgtgggaa gctcgtcatc agcatgatgg tgatcttgac    2580
tccctggcct gtgcccttga agagattggg aggacacaca cgaaactctc aaacatttca    2640
gaatcccagc ttgatgaagc cgacttcaac tacagcaggc aaaatggact ctag           2694
```

<210> SEQ ID NO 14
<211> LENGTH: 897
<212> TYPE: PRT
<213> ORGANISM: homo sapiens

<400> SEQUENCE: 14

```
Met Gly Arg Ala Ala Ala Thr Ala Gly Gly Gly Gly Ala Arg Arg
 1               5                  10                  15

Trp Leu Pro Trp Leu Gly Leu Cys Phe Trp Ala Ala Gly Thr Ala Ala
            20                  25                  30

Ala Arg Gly Thr Asp Asn Gly Glu Ala Leu Pro Glu Ser Ile Pro Ser
        35                  40                  45

Ala Pro Gly Thr Leu Pro His Phe Ile Glu Glu Pro Asp Asp Ala Tyr
    50                  55                  60

Ile Ile Lys Ser Asn Pro Ile Ala Leu Arg Cys Lys Ala Arg Pro Ala
65                  70                  75                  80
```

-continued

```
Met Gln Ile Phe Phe Lys Cys Asn Gly Glu Trp Val His Gln Asn Glu
                85                  90                  95
His Val Ser Glu Glu Thr Leu Asp Glu Ser Ser Gly Leu Lys Val Arg
            100                 105                 110
Glu Val Phe Ile Asn Val Thr Arg Gln Gln Val Glu Asp Phe His Gly
        115                 120                 125
Pro Glu Asp Tyr Trp Cys Gln Cys Val Ala Trp Ser His Leu Gly Thr
    130                 135                 140
Ser Lys Ser Arg Lys Ala Ser Val Arg Ile Ala Tyr Leu Arg Lys Asn
145                 150                 155                 160
Phe Glu Gln Asp Pro Gln Gly Arg Glu Val Pro Ile Glu Gly Met Ile
                165                 170                 175
Val Leu His Cys Arg Pro Pro Glu Gly Val Pro Ala Ala Glu Val Glu
            180                 185                 190
Trp Leu Lys Asn Glu Glu Pro Ile Asp Ser Glu Gln Asp Glu Asn Ile
        195                 200                 205
Asp Thr Arg Ala Asp His Asn Leu Ile Ile Arg Gln Ala Arg Leu Ser
    210                 215                 220
Asp Ser Gly Asn Tyr Thr Cys Met Ala Ala Asn Ile Val Ala Lys Arg
225                 230                 235                 240
Arg Ser Leu Ser Ala Thr Val Val Val Tyr Val Asp Gly Ser Trp Glu
                245                 250                 255
Val Trp Ser Glu Trp Ser Val Cys Ser Pro Glu Cys Glu His Leu Arg
            260                 265                 270
Ile Arg Glu Cys Thr Ala Pro Pro Arg Asn Gly Gly Lys Phe Cys
        275                 280                 285
Glu Gly Leu Ser Gln Glu Ser Glu Asn Cys Thr Asp Gly Leu Cys Ile
    290                 295                 300
Leu Asp Lys Lys Pro Leu His Glu Ile Lys Pro Gln Ser Ile Glu Asn
305                 310                 315                 320
Ala Ser Asp Ile Ala Leu Tyr Ser Gly Leu Gly Ala Ala Val Val Ala
                325                 330                 335
Val Ala Val Leu Val Ile Gly Val Thr Leu Tyr Arg Arg Ser Gln Ser
            340                 345                 350
Asp Tyr Gly Val Asp Val Ile Asp Ser Ser Ala Leu Thr Gly Gly Phe
        355                 360                 365
Gln Thr Phe Asn Phe Lys Thr Val Arg Gln Gly Asn Ser Leu Leu Leu
    370                 375                 380
Asn Ser Ala Met Gln Pro Asp Leu Thr Val Ser Arg Thr Tyr Ser Gly
385                 390                 395                 400
Pro Ile Cys Leu Gln Asp Pro Leu Asp Lys Glu Leu Met Thr Glu Ser
                405                 410                 415
Ser Leu Phe Asn Pro Leu Ser Asp Ile Lys Val Lys Val Gln Ser Ser
            420                 425                 430
Phe Met Val Ser Leu Gly Val Ser Glu Arg Ala Glu Tyr His Gly Lys
        435                 440                 445
Asn His Ser Arg Thr Phe Pro His Gly Asn Asn His Ser Phe Ser Thr
    450                 455                 460
Met His Pro Arg Asn Lys Met Pro Tyr Ile Gln Asn Leu Ser Ser Leu
465                 470                 475                 480
Pro Thr Arg Thr Glu Leu Arg Thr Thr Gly Val Phe Gly His Leu Gly
                485                 490                 495
```

```
Gly Arg Leu Val Met Pro Asn Thr Gly Val Ser Leu Ile Pro His
            500                 505                 510

Gly Ala Ile Pro Glu Asn Ser Trp Glu Ile Tyr Met Ser Ile Asn
            515                 520                 525

Gln Gly Glu Pro Ser Leu Gln Ser Asp Gly Ser Glu Val Leu Leu Ser
530                 535                 540

Pro Glu Val Thr Cys Gly Pro Pro Asp Met Ile Val Thr Thr Pro Phe
545                 550                 555                 560

Ala Leu Thr Ile Pro His Cys Ala Asp Val Ser Ser Glu His Trp Asn
                565                 570                 575

Ile His Leu Lys Lys Arg Thr Gln Gln Gly Lys Trp Glu Glu Val Met
            580                 585                 590

Ser Val Glu Asp Glu Ser Thr Ser Cys Tyr Cys Leu Leu Asp Pro Phe
            595                 600                 605

Ala Cys His Val Leu Leu Asp Ser Phe Gly Thr Tyr Ala Leu Thr Gly
            610                 615                 620

Glu Pro Ile Thr Asp Cys Ala Val Lys Gln Leu Lys Val Ala Val Phe
625                 630                 635                 640

Gly Cys Met Ser Cys Asn Ser Leu Asp Tyr Asn Leu Arg Val Tyr Cys
                645                 650                 655

Val Asp Asn Thr Pro Cys Ala Phe Gln Glu Val Val Ser Asp Glu Arg
                660                 665                 670

His Gln Gly Gly Gln Leu Leu Glu Glu Pro Lys Leu Leu His Phe Lys
            675                 680                 685

Gly Asn Thr Phe Ser Leu Gln Ile Ser Val Leu Asp Ile Pro Pro Phe
            690                 695                 700

Leu Trp Arg Ile Lys Pro Phe Thr Ala Cys Gln Glu Val Pro Phe Ser
705                 710                 715                 720

Arg Val Trp Cys Ser Asn Arg Gln Pro Leu His Cys Ala Phe Ser Leu
                725                 730                 735

Glu Arg Tyr Thr Pro Thr Thr Gln Leu Ser Cys Lys Ile Cys Ile
            740                 745                 750

Arg Gln Leu Lys Gly His Glu Gln Ile Leu Gln Val Gln Thr Ser Ile
            755                 760                 765

Leu Glu Ser Glu Arg Glu Thr Ile Thr Phe Phe Ala Gln Glu Asp Ser
770                 775                 780

Thr Phe Pro Ala Gln Thr Gly Pro Lys Ala Phe Lys Ile Pro Tyr Ser
785                 790                 795                 800

Ile Arg Gln Arg Ile Cys Ala Thr Phe Asp Thr Pro Asn Ala Lys Gly
                805                 810                 815

Lys Asp Trp Gln Met Leu Ala Gln Lys Asn Ser Ile Asn Arg Asn Leu
            820                 825                 830

Ser Tyr Phe Ala Thr Gln Ser Ser Pro Ser Ala Val Ile Leu Asn Leu
835                 840                 845

Trp Glu Ala Arg His Gln His Asp Gly Asp Leu Asp Ser Leu Ala Cys
            850                 855                 860

Ala Leu Glu Glu Ile Gly Arg Thr His Thr Lys Leu Ser Asn Ile Ser
865                 870                 875                 880

Glu Ser Gln Leu Asp Glu Ala Asp Phe Asn Tyr Ser Arg Gln Asn Gly
                885                 890                 895

Leu

<210> SEQ ID NO 15
```

-continued

<211> LENGTH: 2661
<212> TYPE: DNA
<213> ORGANISM: homo sapiens

<400> SEQUENCE: 15

```
atggggagag cggcggccac cgcaggcggc ggcggagggg cgcgccgctg gctcccgtgg      60
ctggggctgt gcttctgggc ggcagggacc gcggctgccc gaggaactga caatggcgaa     120
gcccttcccg aatccatccc atcagctcct ggacactgc ctcatttcat agaggagcca      180
gatgatgctt atattatcaa gagcaaccct attgcactca ggtgcaaagc gaggccagcc     240
atgcagatat tcttcaaatg caacggcgag tgggtccatc agaacgagca cgtctctgaa     300
gagactctgg acgagagctc aggtttgaag gtccgcgaag tgttcatcaa tgttactagg     360
caacaggtgg aggacttcca tgggcccgag gactattggt gccagtgtgt ggcgtggagc     420
cacctgggta cctccaagag caggaaggcc tctgtgcgca tagcctattt acggaaaaac     480
tttgaacaag acccacaagg aagggaagtt cccattgaag catgattgt actgcactgc      540
cgcccaccag agggagtccc tgctgccgag gtggaatggc tgaaaaatga gagcccatt      600
gactctgaac aagacgagaa cattgacacc agggctgacc ataacctgat catcaggcag     660
gcacggctct cggactcagg aaattacacc tgcatggcag ccaacatcgt ggctaagagg     720
agaagcctgt cggccactgt tgtggtctac gtggatggga ctgggaagt gtggagcgaa      780
tggtccgtct gcagtccaga gtgtgaacat ttgcggatcc gggagtgcac agcaccaccc     840
ccgagaaatg gggcaaatt ctgtgaaggt ctaagccagg aatctgaaaa ctgcacagat      900
ggtctttgca tcctaggcat tgagaatgcc agcgacattg ctttgtactc gggcttgggt     960
gctgccgtcg tggccgttgc agtcctggtc attggtgtca ccctttacag acggagccag    1020
agtgactatg gcgtggacgt cattgactct tctgcattga caggtggctt ccagaccttc    1080
aacttcaaaa cagtccgtca aggtaactcc ctgctcctga attctgccat gcagccagat    1140
ctgacagtga gccggacata cagcggaccc atctgtctgc aggaccctct ggacaaggag    1200
ctcatgacag agtcctcact ctttaaccct tgtcggaca tcaaagtgaa agtccagagc     1260
tcgttcatgg tttccctggg agtgtctgag agagctgagt accacggcaa gaatcattcc    1320
aggacttttc cccatggaaa caaccacagc tttagtacaa tgcatcccag aaataaaatg    1380
ccctacatcc aaaatctgtc atcactcccc acaaggacag aactgaggac aactggtgtc    1440
tttggccatt taggggggcg cttagtaatg ccaaatacag gggtgagctt actcatacca    1500
cacggtgcca tcccagagga gaattcttgg gagatttata tgtccatcaa ccaaggtgaa    1560
cccagcctcc agtcagatgg ctctgaggtg ctcctgagtc ctgaagtcac ctgtggtcct    1620
ccagacatga tcgtcaccac tccctttgca ttgaccatcc cgcactgtgc agatgtcagt    1680
tctgagcatt ggaatatcca tttaaagaag aggacacagc agggcaaatg ggaggaagtg    1740
atgtcagtgg aagatgaatc tacatcctgt tactgccttt tggacccctt tgcgtgtcat    1800
gtgctcctgg acagctttgg gacctatgcg ctcactggag agccaatcac agactgtgcc    1860
gtgaagcaac tgaaggtggc ggttttggc tgcatgtcct gtaactccct ggattacaac    1920
ttgagagttt actgtgtgga caataccct tgtgcattc aggaagtggt ttcagatgaa     1980
aggcatcaag gtggacagct cctggaagaa ccaaaattgc tgcatttcaa agggaatacc    2040
tttagtcttc agatttctgt ccttgatatt ccccattcc tctggagaat taaccattc      2100
actgcctgcc aggaagtccc gttctcccgc gtgtggcgca gtaaccggca gccctgcac     2160
tgtgccttct ccctggagcg ttatacgccc actaccaccc agctgtcctg caaaatctgc    2220
```

-continued

```
attcggcagc tcaaaggcca tgaacagatc ctccaagtgc agacatcaat cctagagagt    2280
gaacgagaaa ccatcacttt cttcgcacaa aggacagca ctttccctgc acagactggc    2340
cccaaagcct tcaaaattcc ctactccatc agacagcgga tttgtgctac atttgatacc    2400
cccaatgcca aaggcaagga ctggcagatg ttagcacaga aaaacagcat caacaggaat    2460
ttatcttatt tcgctacaca agtagcccca tctgctgtca ttttgaacct gtgggaagct    2520
cgtcatcagc atgatggtga tcttgactcc ctggcctgtg cccttgaaga gattgggagg    2580
acacacacga aactctcaaa catttcagaa tcccagcttg atgaagccga cttcaactac    2640
agcaggcaaa atggactcta g                                             2661
```

<210> SEQ ID NO 16
<211> LENGTH: 886
<212> TYPE: PRT
<213> ORGANISM: homo sapiens

<400> SEQUENCE: 16

```
Met Gly Arg Ala Ala Thr Ala Gly Gly Gly Gly Ala Arg Arg
1               5                   10                  15

Trp Leu Pro Trp Leu Gly Leu Cys Phe Trp Ala Ala Gly Thr Ala Ala
            20                  25                  30

Ala Arg Gly Thr Asp Asn Gly Glu Ala Leu Pro Glu Ser Ile Pro Ser
        35                  40                  45

Ala Pro Gly Thr Leu Pro His Phe Ile Glu Glu Pro Asp Asp Ala Tyr
    50                  55                  60

Ile Ile Lys Ser Asn Pro Ile Ala Leu Arg Cys Lys Ala Arg Pro Ala
65                  70                  75                  80

Met Gln Ile Phe Phe Lys Cys Asn Gly Glu Trp Val His Gln Asn Glu
                85                  90                  95

His Val Ser Glu Glu Thr Leu Asp Glu Ser Ser Gly Leu Lys Val Arg
            100                 105                 110

Glu Val Phe Ile Asn Val Thr Arg Gln Gln Val Glu Asp Phe His Gly
        115                 120                 125

Pro Glu Asp Tyr Trp Cys Gln Cys Val Ala Trp Ser His Leu Gly Thr
    130                 135                 140

Ser Lys Ser Arg Lys Ala Ser Val Arg Ile Ala Tyr Leu Arg Lys Asn
145                 150                 155                 160

Phe Glu Gln Asp Pro Gln Gly Arg Glu Val Pro Ile Glu Gly Met Ile
                165                 170                 175

Val Leu His Cys Arg Pro Pro Glu Gly Val Pro Ala Ala Glu Val Glu
            180                 185                 190

Trp Leu Lys Asn Glu Glu Pro Ile Asp Ser Glu Gln Asp Glu Asn Ile
        195                 200                 205

Asp Thr Arg Ala Asp His Asn Leu Ile Ile Arg Gln Ala Arg Leu Ser
    210                 215                 220

Asp Ser Gly Asn Tyr Thr Cys Met Ala Ala Asn Ile Val Ala Lys Arg
225                 230                 235                 240

Arg Ser Leu Ser Ala Thr Val Val Tyr Val Asp Gly Ser Trp Glu
                245                 250                 255

Val Trp Ser Glu Trp Ser Val Cys Ser Pro Glu Cys Glu His Leu Arg
            260                 265                 270

Ile Arg Glu Cys Thr Ala Pro Pro Arg Asn Gly Gly Lys Phe Cys
        275                 280                 285
```

```
Glu Gly Leu Ser Gln Glu Ser Glu Asn Cys Thr Asp Gly Leu Cys Ile
    290                 295                 300
Leu Gly Ile Glu Asn Ala Ser Asp Ile Ala Leu Tyr Ser Gly Leu Gly
305                 310                 315                 320
Ala Ala Val Val Ala Val Ala Val Leu Val Ile Gly Val Thr Leu Tyr
                325                 330                 335
Arg Arg Ser Gln Ser Asp Tyr Gly Val Asp Val Ile Asp Ser Ser Ala
            340                 345                 350
Leu Thr Gly Gly Phe Gln Thr Phe Asn Phe Lys Thr Val Arg Gln Gly
        355                 360                 365
Asn Ser Leu Leu Leu Asn Ser Ala Met Gln Pro Asp Leu Thr Val Ser
    370                 375                 380
Arg Thr Tyr Ser Gly Pro Ile Cys Leu Gln Asp Pro Leu Asp Lys Glu
385                 390                 395                 400
Leu Met Thr Glu Ser Ser Leu Phe Asn Pro Leu Ser Asp Ile Lys Val
                405                 410                 415
Lys Val Gln Ser Ser Phe Met Val Ser Leu Gly Val Ser Glu Arg Ala
            420                 425                 430
Glu Tyr His Gly Lys Asn His Ser Arg Thr Phe Pro His Gly Asn Asn
        435                 440                 445
His Ser Phe Ser Thr Met His Pro Arg Asn Lys Met Pro Tyr Ile Gln
    450                 455                 460
Asn Leu Ser Ser Leu Pro Thr Arg Thr Glu Leu Arg Thr Thr Gly Val
465                 470                 475                 480
Phe Gly His Leu Gly Gly Arg Leu Val Met Pro Asn Thr Gly Val Ser
                485                 490                 495
Leu Leu Ile Pro His Gly Ala Ile Pro Glu Glu Asn Ser Trp Glu Ile
            500                 505                 510
Tyr Met Ser Ile Asn Gln Gly Glu Pro Ser Leu Gln Ser Asp Gly Ser
        515                 520                 525
Glu Val Leu Leu Ser Pro Glu Val Thr Cys Gly Pro Pro Asp Met Ile
    530                 535                 540
Val Thr Thr Pro Phe Ala Leu Thr Ile Pro His Cys Ala Asp Val Ser
545                 550                 555                 560
Ser Glu His Trp Asn Ile His Leu Lys Lys Arg Thr Gln Gln Gly Lys
                565                 570                 575
Trp Glu Glu Val Met Ser Val Glu Asp Glu Ser Thr Ser Cys Tyr Cys
            580                 585                 590
Leu Leu Asp Pro Phe Ala Cys His Val Leu Leu Asp Ser Phe Gly Thr
        595                 600                 605
Tyr Ala Leu Thr Gly Glu Pro Ile Thr Asp Cys Ala Val Lys Gln Leu
    610                 615                 620
Lys Val Ala Val Phe Gly Cys Met Ser Cys Asn Ser Leu Asp Tyr Asn
625                 630                 635                 640
Leu Arg Val Tyr Cys Val Asp Asn Thr Pro Cys Ala Phe Gln Glu Val
                645                 650                 655
Val Ser Asp Glu Arg His Gln Gly Gly Leu Leu Glu Glu Pro Lys
            660                 665                 670
Leu Leu His Phe Lys Gly Asn Thr Phe Ser Leu Gln Ile Ser Val Leu
        675                 680                 685
Asp Ile Pro Pro Phe Leu Trp Arg Ile Lys Pro Phe Thr Ala Cys Gln
    690                 695                 700
Glu Val Pro Phe Ser Arg Val Trp Cys Ser Asn Arg Gln Pro Leu His
```

```
                          705                 710                 715                 720
Cys Ala Phe Ser Leu Glu Arg Tyr Thr Pro Thr Thr Gln Leu Ser
                    725                 730                 735
Cys Lys Ile Cys Ile Arg Gln Leu Lys Gly His Glu Gln Ile Leu Gln
                    740                 745                 750
Val Gln Thr Ser Ile Leu Glu Ser Glu Arg Glu Thr Ile Thr Phe Phe
                    755                 760                 765
Ala Gln Glu Asp Ser Thr Phe Pro Ala Gln Thr Gly Pro Lys Ala Phe
                    770                 775                 780
Lys Ile Pro Tyr Ser Ile Arg Gln Arg Ile Cys Ala Thr Phe Asp Thr
785                 790                 795                 800
Pro Asn Ala Lys Gly Lys Asp Trp Gln Met Leu Ala Gln Lys Asn Ser
                    805                 810                 815
Ile Asn Arg Asn Leu Ser Tyr Phe Ala Thr Gln Ser Ser Pro Ser Ala
                    820                 825                 830
Val Ile Leu Asn Leu Trp Glu Ala Arg His Gln His Asp Gly Asp Leu
                    835                 840                 845
Asp Ser Leu Ala Cys Ala Leu Glu Glu Ile Gly Arg Thr His Thr Lys
                    850                 855                 860
Leu Ser Asn Ile Ser Glu Ser Gln Leu Asp Glu Ala Asp Phe Asn Tyr
865                 870                 875                 880
Ser Arg Gln Asn Gly Leu
                    885

<210> SEQ ID NO 17
<211> LENGTH: 1041
<212> TYPE: DNA
<213> ORGANISM: homo sapiens

<400> SEQUENCE: 17
atggcagcca acatcgtggc taagaggaga agcctgtcgg ccactgttgt ggtctacgtg      60
gatgggagct gggaagtgtg gagcgaatgg tccgtctgca gtccagagtg tgaacatttg     120
cggatccggg agtgcacagc accaccccg agaaatgggg gcaaattctg tgaaggtcta     180
agccaggaat ctgaaaactg cacagatggt ctttgcatcc tagataaaaa acctcttcat     240
gaaataaaac cccaaagcat tgagaatgcc agcgacattg cttgtactc gggcttgggt     300 gctgccgtcg tggccgttgc agtcctggtc attggtgtca cccctttacag acggagccag     360 agtgactatg gcgtggacgt cattgactct tctgcattga caggtggctt ccagaccttc     420
aacttcaaaa cagtccgtca agccaagaat atcatggaac taatgataca agaaaaatcc     480
tttggtaact ccctgctcct gaattctgcc atgcagccag atctgacagt gagccggaca     540
tacagcggac ccatctgtct gcaggaccct ctggacaagg agctcatgac agagtcctca     600
ctctttaacc ctttgtcgga catcaaagtg aaagtccaga gctcgttcat ggtttccctg     660
ggagtgtctg agagagctga gtaccacggc aagaatcatt ccaggacttt tccccatgga     720
aacaaccaca gctttagtac aatgcatccc agaaataaaa tgccctacat ccaaaatctg     780
tcatcactcc ccacaaggac agaactgagg acaactggtg tctttggcca tttaggggg     840 cgcttagtaa tgccaaatac aggggtgagc ttactcatac cacacggtgc catcccagag     900
gagaattctt gggagattta tgtccatc aaccaaggtg aacccagtga aaatccagca     960
aacaaaggat caaatagctt gttgaagaac acatatgcca ttgggggaaa aataagcaga    1020 catctggggtt cttctcgctg a                                             1041
```

```
<210> SEQ ID NO 18
<211> LENGTH: 346
<212> TYPE: PRT
<213> ORGANISM: homo sapiens

<400> SEQUENCE: 18

Met Ala Asn Ile Val Ala Lys Arg Arg Ser Leu Ser Ala Thr Val
 1               5                  10                  15

Val Val Tyr Val Asp Gly Ser Trp Glu Val Trp Ser Glu Trp Ser Val
                 20                  25                  30

Cys Ser Pro Glu Cys Glu His Leu Arg Ile Arg Glu Cys Thr Ala Pro
             35                  40                  45

Pro Pro Arg Asn Gly Gly Lys Phe Cys Glu Gly Leu Ser Gln Glu Ser
     50                  55                  60

Glu Asn Cys Thr Asp Gly Leu Cys Ile Leu Asp Lys Lys Pro Leu His
 65                  70                  75                  80

Glu Ile Lys Pro Gln Ser Ile Glu Asn Ala Ser Asp Ile Ala Leu Tyr
                 85                  90                  95

Ser Gly Leu Gly Ala Ala Val Val Ala Val Ala Val Leu Val Ile Gly
                100                 105                 110

Val Thr Leu Tyr Arg Arg Ser Gln Ser Asp Tyr Gly Val Asp Val Ile
            115                 120                 125

Asp Ser Ser Ala Leu Thr Gly Gly Phe Gln Thr Phe Asn Phe Lys Thr
    130                 135                 140

Val Arg Gln Ala Lys Asn Ile Met Glu Leu Met Ile Gln Glu Lys Ser
145                 150                 155                 160

Phe Gly Asn Ser Leu Leu Leu Asn Ser Ala Met Gln Pro Asp Leu Thr
                165                 170                 175

Val Ser Arg Thr Tyr Ser Gly Pro Ile Cys Leu Gln Asp Pro Leu Asp
            180                 185                 190

Lys Glu Leu Met Thr Glu Ser Ser Leu Phe Asn Pro Leu Ser Asp Ile
    195                 200                 205

Lys Val Lys Val Gln Ser Ser Phe Met Val Ser Leu Gly Val Ser Glu
210                 215                 220

Arg Ala Glu Tyr His Gly Lys Asn His Ser Arg Thr Phe Pro His Gly
225                 230                 235                 240

Asn Asn His Ser Phe Ser Thr Met His Pro Arg Asn Lys Met Pro Tyr
                245                 250                 255

Ile Gln Asn Leu Ser Ser Leu Pro Thr Arg Thr Glu Leu Arg Thr Thr
            260                 265                 270

Gly Val Phe Gly His Leu Gly Gly Arg Leu Val Met Pro Asn Thr Gly
    275                 280                 285

Val Ser Leu Leu Ile Pro His Gly Ala Ile Pro Glu Glu Asn Ser Trp
290                 295                 300

Glu Ile Tyr Met Ser Ile Asn Gln Gly Glu Pro Ser Glu Asn Pro Ala
305                 310                 315                 320

Asn Lys Gly Ser Asn Ser Leu Leu Lys Asn Thr Tyr Ala Ile Gly Gly
                325                 330                 335

Lys Ile Ser Arg His Leu Gly Ser Ser Arg
            340                 345

<210> SEQ ID NO 19
<211> LENGTH: 1008
<212> TYPE: DNA
```

-continued

<213> ORGANISM: homo sapiens

<400> SEQUENCE: 19

```
atggcagcca acatcgtggc taagaggaga agcctgtcgg ccactgttgt ggtctacgtg      60
gatgggagct gggaagtgtg gagcgaatgg tccgtctgca gtccagagtg tgaacatttg     120
cggatccggg agtgcacagc accaccccg agaaatgggg gcaaattctg tgaaggtcta      180
agccaggaat ctgaaaactg cacagatggt ctttgcatcc taggcattga aaatgccagc     240
gacattgctt tgtactcggg cttgggtgct gccgtcgtgg ccgttgcagt cctggtcatt     300
ggtgtcaccc tttacagacg gagccagagt gactatggcg tggacgtcat tgactcttct     360
gcattgacag gtggcttcca gaccttcaac ttcaaaacag tccgtcaagc caagaatatc     420
atggaactaa tgatacaaga aaatcctttg gtaactccc tgctcctgaa ttctgccatg      480
cagccagatc tgacagtgag ccggacatac agcggaccca tctgtctgca ggaccctctg     540
gacaaggagc tcatgacaga gtcctcactc tttaacccct tgtcggacat caaagtgaaa    600
gtccagagct cgttcatggt ttccctggga gtgtctgaga gagctgagta ccacggcaag     660
aatcattcca ggactttcc ccatggaaac aaccacagct ttagtacaat gcatcccaga      720
aataaaatgc cctacatcca aaatctgtca tcactcccca caaggacaga actgaggaca     780
actggtgtct ttggccattt aggggggcgc ttagtaatgc caaatacagg ggtgagctta     840
ctcataccac acggtgccat cccagaggag aattcttggg agattatat gtccatcaac      900
caaggtgaac ccagtgaaaa tccagcaaac aaaggatcaa atagcttgtt gaagaacaca     960
tatgccattg ggggaaaaat aagcagacat ctgggttctt ctcgctga              1008
```

<210> SEQ ID NO 20
<211> LENGTH: 335
<212> TYPE: PRT
<213> ORGANISM: homo sapiens

<400> SEQUENCE: 20

```
Met Ala Ala Asn Ile Val Ala Lys Arg Arg Ser Leu Ser Ala Thr Val
 1               5                  10                  15
Val Val Tyr Val Asp Gly Ser Trp Glu Val Trp Ser Glu Trp Ser Val
            20                  25                  30
Cys Ser Pro Glu Cys Glu His Leu Arg Ile Arg Glu Cys Thr Ala Pro
        35                  40                  45
Pro Pro Arg Asn Gly Gly Lys Phe Cys Glu Gly Leu Ser Gln Glu Ser
    50                  55                  60
Glu Asn Cys Thr Asp Gly Leu Cys Ile Leu Gly Ile Glu Asn Ala Ser
65                  70                  75                  80
Asp Ile Ala Leu Tyr Ser Gly Leu Gly Ala Ala Val Val Ala Val Ala
                85                  90                  95
Val Leu Val Ile Gly Val Thr Leu Tyr Arg Arg Ser Gln Ser Asp Tyr
            100                 105                 110
Gly Val Asp Val Ile Asp Ser Ser Ala Leu Thr Gly Gly Phe Gln Thr
        115                 120                 125
Phe Asn Phe Lys Thr Val Arg Gln Ala Lys Asn Ile Met Glu Leu Met
    130                 135                 140
Ile Gln Glu Lys Ser Phe Gly Asn Ser Leu Leu Leu Asn Ser Ala Met
145                 150                 155                 160
Gln Pro Asp Leu Thr Val Ser Arg Thr Tyr Ser Gly Pro Ile Cys Leu
                165                 170                 175
```

```
Gln Asp Pro Leu Asp Lys Glu Leu Met Thr Glu Ser Ser Leu Phe Asn
            180                 185                 190
Pro Leu Ser Asp Ile Lys Val Lys Val Gln Ser Ser Phe Met Val Ser
        195                 200                 205
Leu Gly Val Ser Glu Arg Ala Glu Tyr His Gly Lys Asn His Ser Arg
    210                 215                 220
Thr Phe Pro His Gly Asn Asn His Ser Phe Ser Thr Met His Pro Arg
225                 230                 235                 240
Asn Lys Met Pro Tyr Ile Gln Asn Leu Ser Ser Leu Pro Thr Arg Thr
                245                 250                 255
Glu Leu Arg Thr Thr Gly Val Phe Gly His Leu Gly Arg Leu Val
            260                 265                 270
Met Pro Asn Thr Gly Val Ser Leu Leu Ile Pro His Gly Ala Ile Pro
        275                 280                 285
Glu Glu Asn Ser Trp Glu Ile Tyr Met Ser Ile Asn Gln Gly Glu Pro
    290                 295                 300
Ser Glu Asn Pro Ala Asn Lys Gly Ser Asn Ser Leu Leu Lys Asn Thr
305                 310                 315                 320
Tyr Ala Ile Gly Gly Lys Ile Ser Arg His Leu Gly Ser Ser Arg
                325                 330                 335

<210> SEQ ID NO 21
<211> LENGTH: 999
<212> TYPE: DNA
<213> ORGANISM: homo sapiens

<400> SEQUENCE: 21
atggcagcca acatcgtggc taagaggaga agcctgtcgg ccactgttgt ggtctacgtg      60
gatgggagct gggaagtgtg gagcgaatgg tccgtctgca gtccagagtg tgaacatttg     120
cggatccggg agtgcacagc accaccccccg agaaatgggg gcaaattctg tgaaggtcta     180
agccaggaat ctgaaaactg cacagatggt ctttgcatcc tagataaaaa acctcttcat     240
gaaataaaac cccaaagcat tgagaatgcc agcgacattg cttttgtactc gggcttgggt    300 gctgccgtcg tggccgttgc agtcctggtc attggtgtca ccctttacag acggagccag    360
agtgactatg gcgtggacgt cattgactct tctgcattga caggtggctt ccagaccttc    420
aacttcaaaa cagtccgtca aggtaactcc ctgctcctga attctgccat gcagccagat    480
ctgacagtga gccggacata cagcggaccc atctgtctgc aggaccctct ggacaaggag    540
ctcatgacag agtcctcact ctttaaccct tgtcggaca tcaaagtgaa agtccagagc     600
tcgttcatgg tttccctggg agtgtctgag agagctgagt accacggcaa gaatcattcc    660
aggactttcc cccatggaaa caaccacagc tttagtacaa tgcatcccag aaataaaatg    720
ccctacatcc aaaatctgtc atcactcccc acaaggacag aactgaggac aactggtgtc    780
tttggccatt taggggggcg cttagtaatg ccaaatacag gggtgagctt actcatacca    840
cacggtgcca tcccagagga gaattcttgg gagatttata tgtccatcaa ccaaggtgaa    900
cccagtgaaa atccagcaaa caaaggatca aatagcttgt tgaagaacac atatgccatt    960
gggggaaaaa taagcagaca tctgggttct ctcgctga                             999

<210> SEQ ID NO 22
<211> LENGTH: 332
<212> TYPE: PRT
<213> ORGANISM: homo sapiens

<400> SEQUENCE: 22
```

-continued

```
Met Ala Ala Asn Ile Val Ala Lys Arg Arg Ser Leu Ser Ala Thr Val
 1               5                  10                 15

Val Val Tyr Val Asp Gly Ser Trp Glu Val Trp Ser Glu Trp Ser Val
            20                  25                 30

Cys Ser Pro Glu Cys Glu His Leu Arg Ile Arg Glu Cys Thr Ala Pro
        35                  40                 45

Pro Pro Arg Asn Gly Gly Lys Phe Cys Glu Gly Leu Ser Gln Glu Ser
    50                  55                 60

Glu Asn Cys Thr Asp Gly Leu Cys Ile Leu Asp Lys Lys Pro Leu His
65                  70                 75                  80

Glu Ile Lys Pro Gln Ser Ile Glu Asn Ala Ser Asp Ile Ala Leu Tyr
                85                  90                 95

Ser Gly Leu Gly Ala Ala Val Val Val Ala Val Leu Val Ile Gly
            100                 105                110

Val Thr Leu Tyr Arg Arg Ser Gln Ser Asp Tyr Gly Val Asp Val Ile
            115                 120                125

Asp Ser Ser Ala Leu Thr Gly Gly Phe Gln Thr Phe Asn Phe Lys Thr
130                 135                 140

Val Arg Gln Gly Asn Ser Leu Leu Leu Asn Ser Ala Met Gln Pro Asp
145                 150                 155                160

Leu Thr Val Ser Arg Thr Tyr Ser Gly Pro Ile Cys Leu Gln Asp Pro
                165                 170                175

Leu Asp Lys Glu Leu Met Thr Glu Ser Ser Leu Phe Asn Pro Leu Ser
            180                 185                 190

Asp Ile Lys Val Lys Val Gln Ser Ser Phe Met Val Ser Leu Gly Val
            195                 200                 205

Ser Glu Arg Ala Glu Tyr His Gly Lys Asn His Ser Arg Thr Phe Pro
210                 215                 220

His Gly Asn Asn His Ser Phe Ser Thr Met His Pro Arg Asn Lys Met
225                 230                 235                240

Pro Tyr Ile Gln Asn Leu Ser Ser Leu Pro Thr Arg Thr Glu Leu Arg
                245                 250                 255

Thr Thr Gly Val Phe Gly His Leu Gly Gly Arg Leu Val Met Pro Asn
            260                 265                 270

Thr Gly Val Ser Leu Leu Ile Pro His Gly Ala Ile Pro Glu Glu Asn
            275                 280                 285

Ser Trp Glu Ile Tyr Met Ser Ile Asn Gln Gly Glu Pro Ser Glu Asn
290                 295                 300

Pro Ala Asn Lys Gly Ser Asn Ser Leu Leu Lys Asn Thr Tyr Ala Ile
305                 310                 315                320

Gly Gly Lys Ile Ser Arg His Leu Gly Ser Ser Arg
                325                 330
```

<210> SEQ ID NO 23
<211> LENGTH: 966
<212> TYPE: DNA
<213> ORGANISM: homo sapiens

<400> SEQUENCE: 23

```
atggcagcca acatcgtggc taagaggaga agcctgtcgg ccactgttgt ggtctacgtg      60
gatgggagct gggaagtgtg gagcgaatgg tccgtctgca gtccagagtg tgaacatttg     120
cggatccggg agtgcacagc accacccccg agaaatgggg gcaaattctg tgaaggtcta     180
agccaggaat ctgaaaactg cacagatggt ctttgcatcc taggcattga aatgccagc      240
```

-continued

```
gacattgctt tgtactcggg cttgggtgct gccgtcgtgg ccgttgcagt cctggtcatt    300
ggtgtcaccc tttacagacg gagccagagt gactatggcg tggacgtcat tgactcttct    360
gcattgacag gtggcttcca gaccttcaac ttcaaaacag tccgtcaagg taactccctg    420
ctcctgaatt ctgccatgca gccagatctg acagtgagcc ggacatacag cggacccatc    480
tgtctgcagg accctctgga caaggagctc atgacagagt cctcactctt taacccttg    540
tcggacatca aagtgaaagt ccagagctcg ttcatggttt ccctgggagt gtctgagaga    600
gctgagtacc acggcaagaa tcattccagg acttttcccc atggaaacaa ccacagcttt    660
agtacaatgc atcccagaaa taaaatgccc tacatccaaa atctgtcatc actccccaca    720
aggacagaac tgaggacaac tggtgtcttt ggccatttag gggggcgctt agtaatgcca    780
aatacagggg tgagcttact cataccacac ggtgccatcc cagaggagaa ttcttgggag    840
atttatatgt ccatcaacca aggtgaaccc agtgaaaatc cagcaaacaa aggatcaaat    900
agcttgttga agaacacata tgccattggg ggaaaaataa gcagacatct gggttcttct    960
cgctga                                                                966
```

<210> SEQ ID NO 24
<211> LENGTH: 321
<212> TYPE: PRT
<213> ORGANISM: homo sapiens

<400> SEQUENCE: 24

```
Met Ala Ala Asn Ile Val Ala Lys Arg Arg Ser Leu Ser Ala Thr Val
  1               5                  10                  15

Val Val Tyr Val Asp Gly Ser Trp Glu Val Trp Ser Glu Trp Ser Val
             20                  25                  30

Cys Ser Pro Glu Cys Glu His Leu Arg Ile Arg Glu Cys Thr Ala Pro
         35                  40                  45

Pro Pro Arg Asn Gly Gly Lys Phe Cys Glu Gly Leu Ser Gln Glu Ser
     50                  55                  60

Glu Asn Cys Thr Asp Gly Leu Cys Ile Leu Gly Ile Glu Asn Ala Ser
 65                  70                  75                  80

Asp Ile Ala Leu Tyr Ser Gly Leu Gly Ala Val Val Ala Val Ala
                 85                  90                  95

Val Leu Val Ile Gly Val Thr Leu Tyr Arg Arg Ser Gln Ser Asp Tyr
                100                 105                 110

Gly Val Asp Val Ile Asp Ser Ser Ala Leu Thr Gly Gly Phe Gln Thr
            115                 120                 125

Phe Asn Phe Lys Thr Val Arg Gln Gly Asn Ser Leu Leu Leu Asn Ser
        130                 135                 140

Ala Met Gln Pro Asp Leu Thr Val Ser Arg Thr Tyr Ser Gly Pro Ile
145                 150                 155                 160

Cys Leu Gln Asp Pro Leu Asp Lys Glu Leu Met Thr Glu Ser Ser Leu
                165                 170                 175

Phe Asn Pro Leu Ser Asp Ile Lys Val Lys Val Gln Ser Ser Phe Met
            180                 185                 190

Val Ser Leu Gly Val Ser Glu Arg Ala Glu Tyr His Gly Lys Asn His
        195                 200                 205

Ser Arg Thr Phe Pro His Gly Asn Asn His Ser Phe Ser Thr Met His
    210                 215                 220

Pro Arg Asn Lys Met Pro Tyr Ile Gln Asn Leu Ser Ser Leu Pro Thr
225                 230                 235                 240
```

```
Arg Thr Glu Leu Arg Thr Thr Gly Val Phe Gly His Leu Gly Arg
            245                 250                 255

Leu Val Met Pro Asn Thr Gly Val Ser Leu Leu Ile Pro His Gly Ala
            260                 265                 270

Ile Pro Glu Glu Asn Ser Trp Glu Ile Tyr Met Ser Ile Asn Gln Gly
        275                 280                 285

Glu Pro Ser Glu Asn Pro Ala Asn Lys Gly Ser Asn Ser Leu Leu Lys
        290                 295                 300

Asn Thr Tyr Ala Ile Gly Gly Lys Ile Ser Arg His Leu Gly Ser Ser
305                 310                 315                 320

Arg

<210> SEQ ID NO 25
<211> LENGTH: 2043
<212> TYPE: DNA
<213> ORGANISM: homo sapiens

<400> SEQUENCE: 25
atggcagcca acatcgtggc taagaggaga agcctgtcgg ccactgttgt ggtctacgtg      60
gatgggagct gggaagtgtg gagcgaatgg tccgtctgca gtccagagtg tgaacatttg     120
cggatccggg agtgcacagc accaccccg agaaatgggg gcaaattctg tgaaggtcta     180
agccaggaat ctgaaaactg cacagatggt ctttgcatcc tagataaaaa acctcttcat     240
gaaataaaac cccaaagcat tgagaatgcc agcgacattg ctttgtactc gggcttgggt     300
gctgccgtcg tggccgttgc agtcctggtc attggtgtca cccttacag acggagccag     360
agtgactatg gcgtggacgt cattgactct tctgcattga caggtggctt ccagaccttc     420
aacttcaaaa cagtccgtca agccaagaat atcatggaac taatgataca gaaaaatcc     480
tttggtaact ccctgctcct gaattctgcc atgcagccag atctgacagt gagccggaca     540
tacagcggac ccatctgtct gcaggaccct ctggacaagg agctcatgac agagtcctca     600
ctctttaacc ctttgtcgga catcaaagtg aaagtccaga gctcgttcat ggtttccctg     660
ggagtgtctg agagagctga gtaccacggc aagaatcatt ccaggacttt tccccatgga     720
aacaaccaca gctttagtac aatgcatccc agaaataaaa tgccctacat ccaaaatctg     780
tcatcactcc ccacaaggac agaactgagg acaactggtg tctttggcca tttagggggg     840
cgcttagtaa tgccaaatac aggggtgagc ttactcatac acacggtgc catcccagag     900
gagaattctt gggagattta tgtccatca accaaggtg aacccagcct ccagtcagat     960
ggctctgagg tgctcctgag tcctgaagtc acctgtggtc ctccagacat gatcgtcacc    1020
actccctttg cattgaccat cccgcactgt gcagatgtca gttctgagca ttggaatatc    1080
catttaaaga gaggacaca gcagggcaaa tgggaggaag tgatgtcagt ggaagatgaa    1140
tctacatcct gttactgcct tttggacccc tttgcgtgtc atgtgctcct ggacagcttt    1200
gggacctatg cgctcactgg agagccaatc acagactgtg ccgtgaagca actgaaggtg    1260
gcggttttg ctgcatgtc ctgtaactcc ctggattaca acttgagagt ttactgtgtg    1320
gacaataccc cttgtgcatt tcaggaagtg gtttcagatg aaaggcatca aggtggacag    1380
ctcctggaag aaccaaaatt gctgcatttc aaagggaata cctttagtct tcagatttct    1440
gtccttgata ttcccccatt cctctggaga attaaaccat tcactgcctg ccaggaagtc    1500
ccgttctccc gcgtgtggtg cagtaaccgg cagcccctgc actgtgcctt ctccctggag    1560
cgttatacgc ccactaccac ccagctgtcc tgcaaaatct gcattcggca gctcaaaggc    1620
```

-continued

```
catgaacaga tcctccaagt gcagacatca atcctagaga gtgaacgaga aaccatcact    1680
ttcttcgcac aagaggacag cactttccct gcacagactg gccccaaagc cttcaaaatt    1740
ccctactcca tcagacagcg gatttgtgct acatttgata cccccaatgc caaaggcaag    1800
gactggcaga tgttagcaca gaaaaacagc atcaacagga atttatctta tttcgctaca    1860
caaagtagcc atctgctgt cattttgaac ctgtgggaag ctcgtcatca gcatgatggt    1920
gatcttgact ccctggcctg tgcccttgaa gagattggga ggacacacac gaaactctca    1980
aacatttcag aatcccagct tgatgaagcc gacttcaact acagcaggca aaatggactc    2040
tag                                                                 2043
```

<210> SEQ ID NO 26
<211> LENGTH: 680
<212> TYPE: PRT
<213> ORGANISM: homo sapiens

<400> SEQUENCE: 26

```
Met Ala Ala Asn Ile Val Ala Lys Arg Arg Ser Leu Ser Ala Thr Val
 1               5                  10                  15

Val Val Tyr Val Asp Gly Ser Trp Glu Val Trp Ser Glu Trp Ser Val
                20                  25                  30

Cys Ser Pro Glu Cys Glu His Leu Arg Ile Arg Glu Cys Thr Ala Pro
            35                  40                  45

Pro Pro Arg Asn Gly Gly Lys Phe Cys Glu Gly Leu Ser Gln Glu Ser
        50                  55                  60

Glu Asn Cys Thr Asp Gly Leu Cys Ile Leu Asp Lys Lys Pro Leu His
65                  70                  75                  80

Glu Ile Lys Pro Gln Ser Ile Glu Asn Ala Ser Asp Ile Ala Leu Tyr
                85                  90                  95

Ser Gly Leu Gly Ala Ala Val Val Ala Val Ala Val Leu Val Ile Gly
            100                 105                 110

Val Thr Leu Tyr Arg Arg Ser Gln Ser Asp Tyr Gly Val Asp Val Ile
        115                 120                 125

Asp Ser Ser Ala Leu Thr Gly Gly Phe Gln Thr Phe Asn Phe Lys Thr
    130                 135                 140

Val Arg Gln Ala Lys Asn Ile Met Glu Leu Met Ile Gln Glu Lys Ser
145                 150                 155                 160

Phe Gly Asn Ser Leu Leu Leu Asn Ser Ala Met Gln Pro Asp Leu Thr
                165                 170                 175

Val Ser Arg Thr Tyr Ser Gly Pro Ile Cys Leu Gln Asp Pro Leu Asp
            180                 185                 190

Lys Glu Leu Met Thr Glu Ser Ser Leu Phe Asn Pro Leu Ser Asp Ile
        195                 200                 205

Lys Val Lys Val Gln Ser Ser Phe Met Val Ser Leu Gly Val Ser Glu
    210                 215                 220

Arg Ala Glu Tyr His Gly Lys Asn His Ser Arg Thr Phe Pro His Gly
225                 230                 235                 240

Asn Asn His Ser Phe Ser Thr Met His Pro Arg Asn Lys Met Pro Tyr
                245                 250                 255

Ile Gln Asn Leu Ser Ser Leu Pro Thr Arg Thr Glu Leu Arg Thr Thr
            260                 265                 270

Gly Val Phe Gly His Leu Gly Gly Arg Leu Val Met Pro Asn Thr Gly
        275                 280                 285
```

```
Val Ser Leu Leu Ile Pro His Gly Ala Ile Pro Glu Asn Ser Trp
    290                 295                 300
Glu Ile Tyr Met Ser Ile Asn Gln Gly Glu Pro Ser Leu Gln Ser Asp
305                 310                 315                 320
Gly Ser Glu Val Leu Leu Ser Pro Glu Val Thr Cys Gly Pro Pro Asp
                325                 330                 335
Met Ile Val Thr Thr Pro Phe Ala Leu Thr Ile Pro His Cys Ala Asp
            340                 345                 350
Val Ser Ser Glu His Trp Asn Ile His Leu Lys Lys Arg Thr Gln Gln
        355                 360                 365
Gly Lys Trp Glu Glu Val Met Ser Val Glu Asp Glu Ser Thr Ser Cys
370                 375                 380
Tyr Cys Leu Leu Asp Pro Phe Ala Cys His Val Leu Leu Asp Ser Phe
385                 390                 395                 400
Gly Thr Tyr Ala Leu Thr Gly Glu Pro Ile Thr Asp Cys Ala Val Lys
                405                 410                 415
Gln Leu Lys Val Ala Val Phe Gly Cys Met Ser Cys Asn Ser Leu Asp
            420                 425                 430
Tyr Asn Leu Arg Val Tyr Cys Val Asp Asn Thr Pro Cys Ala Phe Gln
        435                 440                 445
Glu Val Val Ser Asp Glu Arg His Gln Gly Gly Gln Leu Leu Glu Glu
450                 455                 460
Pro Lys Leu Leu His Phe Lys Gly Asn Thr Phe Ser Leu Gln Ile Ser
465                 470                 475                 480
Val Leu Asp Ile Pro Pro Phe Leu Trp Arg Ile Lys Pro Phe Thr Ala
                485                 490                 495
Cys Gln Glu Val Pro Phe Ser Arg Val Trp Cys Ser Asn Arg Gln Pro
            500                 505                 510
Leu His Cys Ala Phe Ser Leu Glu Arg Tyr Thr Pro Thr Thr Thr Gln
        515                 520                 525
Leu Ser Cys Lys Ile Cys Ile Arg Gln Leu Lys Gly His Glu Gln Ile
530                 535                 540
Leu Gln Val Gln Thr Ser Ile Leu Glu Ser Arg Glu Thr Ile Thr
545                 550                 555                 560
Phe Phe Ala Gln Glu Asp Ser Thr Phe Pro Ala Gln Thr Gly Pro Lys
                565                 570                 575
Ala Phe Lys Ile Pro Tyr Ser Ile Arg Gln Arg Ile Cys Ala Thr Phe
            580                 585                 590
Asp Thr Pro Asn Ala Lys Gly Lys Asp Trp Gln Met Leu Ala Gln Lys
        595                 600                 605
Asn Ser Ile Asn Arg Asn Leu Ser Tyr Phe Ala Thr Gln Ser Ser Pro
610                 615                 620
Ser Ala Val Ile Leu Asn Leu Trp Glu Ala Arg His Gln His Asp Gly
625                 630                 635                 640
Asp Leu Asp Ser Leu Ala Cys Ala Leu Glu Glu Ile Gly Arg Thr His
                645                 650                 655
Thr Lys Leu Ser Asn Ile Ser Glu Ser Gln Leu Asp Glu Ala Asp Phe
            660                 665                 670
Asn Tyr Ser Arg Gln Asn Gly Leu
        675                 680

<210> SEQ ID NO 27
<211> LENGTH: 2010
<212> TYPE: DNA
```

-continued

<213> ORGANISM: homo sapiens

<400> SEQUENCE: 27

```
atggcagcca acatcgtggc taagaggaga agcctgtcgg ccactgttgt ggtctacgtg      60
gatgggagct gggaagtgtg gagcgaatgg tccgtctgca gtccagagtg tgaacatttg     120
cggatccggg agtgcacagc accaccccg agaaatgggg gcaaattctg tgaaggtcta     180
agccaggaat ctgaaaactg cacagatggt ctttgcatcc taggcattga gaatgccagc     240
gacattgctt tgtactcggg cttgggtgct gccgtcgtgg ccgttgcagt cctggtcatt     300
ggtgtcaccc tttacagacg gagccagagt gactatggcg tggacgtcat tgactcttct     360
gcattgacag gtggcttcca gaccttcaac ttcaaaacag tccgtcaagc caagaatatc     420
atggaactaa tgatacaaga aaaatccttt ggtaactccc tgctcctgaa ttctgccatg     480
cagccagatc tgacagtgag ccggacatac agcggaccca tctgtctgca ggaccctctg     540
gacaaggagc tcatgacaga gtcctcactc tttaacccct tgtcggacat caaagtgaaa     600
gtccagagct cgttcatggt tccctgggga gtgtctgaga gagctgagta ccacggcaag     660
aatcattcca ggacttttcc ccatggaaac aaccacagct tagtacaat gcatcccaga     720
aataaaatgc cctacatcca aaatctgtca tcactcccca caaggacaga actgaggaca     780
actggtgtct ttggccattt agggggcgc ttagtaatgc caaatacagg ggtgagctta     840
ctcataccac acggtgccat cccagaggag aattcttggg agatttatat gtccatcaac     900
caaggtgaac ccagcctcca gtcagatggc tctgaggtgc tcctgagtcc tgaagtcacc     960
tgtggtcctc cagacatgat cgtcaccact ccctttgcat tgaccatccc gcactgtgca    1020
gatgtcagtt ctgagcattg gaatatccat ttaaagaaga ggacacagca gggcaaatgg    1080
gaggaagtga tgtcagtgga agatgaatct acatcctgtt actgcctttt ggacccctt    1140
gcgtgtcatg tgctcctgga cagctttggg acctatgcgc tcactggaga gccaatcaca    1200
gactgtgccg tgaagcaact gaaggtggcg gttttggct gcatgtcctg taactccctg    1260
gattacaact tgagagttta ctgtgtggac aataccccct tgtgcatttca ggaagtggtt    1320
tcagatgaaa ggcatcaagg tggacagctc ctggaagaac caaaattgct gcatttcaaa    1380
gggaatacct ttagtcttca gatttctgtc cttgatattc ccccattcct ctggagaatt    1440
aaaccattca ctgcctgcca ggaagtcccg ttctcccgcg tgtggtgcag taaccggcag    1500
ccctgcact gtgccttctc cctggagcgt tatacgccca ctaccaccca gctgtcctgc    1560
aaaatctgca ttcggcagct caaaggccat gaacagatcc tccaagtgca gacatcaatc    1620
ctagagagtg aacagaaaac catcactttc ttcgcacaag aggacagcac ttttcctgca    1680
cagactggcc ccaaagcctt caaaattccc tactccatca gacagcggat tgtgctacta    1740
tttgatacc ccaatgccaa aggcaaggac tggcagatgt tagcacagaa aaacagcatc    1800
aacaggaatt tatcttattt cgctacacaa agtagcccat ctgctgtcat tttgaacctg    1860
tgggaagctc gtcatcagca tgatggtgat cttgactccc tggcctgtgc ccttgaagag    1920
attgggagga cacacacgaa actctcaaac atttcagaat cccagcttga tgaagccgac    1980
ttcaactaca gcaggcaaaa tggactctag                                       2010
```

<210> SEQ ID NO 28
<211> LENGTH: 669
<212> TYPE: PRT
<213> ORGANISM: homo sapiens

<400> SEQUENCE: 28

-continued

```
Met Ala Ala Asn Ile Val Ala Lys Arg Arg Ser Leu Ser Ala Thr Val
 1               5                  10                  15

Val Val Tyr Val Asp Gly Ser Trp Glu Val Trp Ser Glu Trp Ser Val
            20                  25                  30

Cys Ser Pro Glu Cys Glu His Leu Arg Ile Arg Glu Cys Thr Ala Pro
            35                  40                  45

Pro Pro Arg Asn Gly Gly Lys Phe Cys Glu Gly Leu Ser Gln Glu Ser
    50                  55                  60

Glu Asn Cys Thr Asp Gly Leu Cys Ile Leu Gly Ile Glu Asn Ala Ser
65                  70                  75                  80

Asp Ile Ala Leu Tyr Ser Gly Leu Gly Ala Ala Val Val Ala Val Ala
                85                  90                  95

Val Leu Val Ile Gly Val Thr Leu Tyr Arg Arg Ser Gln Ser Asp Tyr
                100                 105                 110

Gly Val Asp Val Ile Asp Ser Ser Ala Leu Thr Gly Gly Phe Gln Thr
            115                 120                 125

Phe Asn Phe Lys Thr Val Arg Gln Ala Lys Asn Ile Met Glu Leu Met
    130                 135                 140

Ile Gln Glu Lys Ser Phe Gly Asn Ser Leu Leu Leu Asn Ser Ala Met
145                 150                 155                 160

Gln Pro Asp Leu Thr Val Ser Arg Thr Tyr Ser Gly Pro Ile Cys Leu
                165                 170                 175

Gln Asp Pro Leu Asp Lys Glu Leu Met Thr Glu Ser Ser Leu Phe Asn
            180                 185                 190

Pro Leu Ser Asp Ile Lys Val Lys Val Gln Ser Ser Phe Met Val Ser
    195                 200                 205

Leu Gly Val Ser Glu Arg Ala Glu Tyr His Gly Lys Asn His Ser Arg
    210                 215                 220

Thr Phe Pro His Gly Asn Asn His Ser Phe Ser Thr Met His Pro Arg
225                 230                 235                 240

Asn Lys Met Pro Tyr Ile Gln Asn Leu Ser Ser Leu Pro Thr Arg Thr
                245                 250                 255

Glu Leu Arg Thr Thr Gly Val Phe Gly His Leu Gly Gly Arg Leu Val
            260                 265                 270

Met Pro Asn Thr Gly Val Ser Leu Leu Ile Pro His Gly Ala Ile Pro
        275                 280                 285

Glu Glu Asn Ser Trp Glu Ile Tyr Met Ser Ile Asn Gln Gly Glu Pro
    290                 295                 300

Ser Leu Gln Ser Asp Gly Ser Glu Val Leu Leu Ser Pro Glu Val Thr
305                 310                 315                 320

Cys Gly Pro Pro Asp Met Ile Val Thr Thr Pro Phe Ala Leu Thr Ile
                325                 330                 335

Pro His Cys Ala Asp Val Ser Ser Glu His Trp Asn Ile His Leu Lys
            340                 345                 350

Lys Arg Thr Gln Gln Gly Lys Trp Glu Glu Val Met Ser Val Glu Asp
        355                 360                 365

Glu Ser Thr Ser Cys Tyr Cys Leu Leu Asp Pro Phe Ala Cys His Val
    370                 375                 380

Leu Leu Asp Ser Phe Gly Thr Tyr Ala Leu Thr Gly Glu Pro Ile Thr
385                 390                 395                 400

Asp Cys Ala Val Lys Gln Leu Lys Val Ala Val Phe Gly Cys Met Ser
                405                 410                 415
```

| | | | | | | | | | | | | |
|---|---|---|---|---|---|---|---|---|---|---|---|---|
|Cys|Asn|Ser|Leu|Asp|Tyr|Asn|Leu|Arg|Val|Tyr|Cys|Val|Asp|Asn|Thr|
| | | |420| | |425| | | |430| | |

Pro Cys Ala Phe Gln Glu Val Ser Asp Glu Arg His Gln Gly Gly
          435             440             445

Gln Leu Leu Glu Glu Pro Lys Leu Leu His Phe Lys Gly Asn Thr Phe
        450             455             460

Ser Leu Gln Ile Ser Val Leu Asp Ile Pro Pro Phe Leu Trp Arg Ile
465             470             475             480

Lys Pro Phe Thr Ala Cys Gln Glu Val Pro Phe Ser Arg Val Trp Cys
            485             490             495

Ser Asn Arg Gln Pro Leu His Cys Ala Phe Ser Leu Glu Arg Tyr Thr
            500             505             510

Pro Thr Thr Thr Gln Leu Ser Cys Lys Ile Cys Ile Arg Gln Leu Lys
            515             520             525

Gly His Glu Gln Ile Leu Gln Val Gln Thr Ser Ile Leu Glu Ser Glu
        530             535             540

Arg Glu Thr Ile Thr Phe Phe Ala Gln Glu Asp Ser Thr Phe Pro Ala
545             550             555             560

Gln Thr Gly Pro Lys Ala Phe Lys Ile Pro Tyr Ser Ile Arg Gln Arg
            565             570             575

Ile Cys Ala Thr Phe Asp Thr Pro Asn Ala Lys Gly Lys Asp Trp Gln
            580             585             590

Met Leu Ala Gln Lys Asn Ser Ile Asn Arg Asn Leu Ser Tyr Phe Ala
            595             600             605

Thr Gln Ser Ser Pro Ser Ala Val Ile Leu Asn Leu Trp Glu Ala Arg
        610             615             620

His Gln His Asp Gly Asp Leu Asp Ser Leu Ala Cys Ala Leu Glu Glu
625             630             635             640

Ile Gly Arg Thr His Thr Lys Leu Ser Asn Ile Ser Glu Ser Gln Leu
            645             650             655

Asp Glu Ala Asp Phe Asn Tyr Ser Arg Gln Asn Gly Leu
            660             665

<210> SEQ ID NO 29
<211> LENGTH: 2001
<212> TYPE: DNA
<213> ORGANISM: homo sapiens

<400> SEQUENCE: 29

| | | |
|---|---|---|
|atggcagcca acatcgtggc taagaggaga agcctgtcgg ccactgttgt ggtctacgtg|60|
|gatgggagct gggaagtgtg gagcgaatgg tccgtctgca gtccagagtg tgaacatttg|120|
|cggatccggg agtgcacagc accaccccg agaaatgggg gcaaattctg tgaaggtcta|180|
|agccaggaat ctgaaaactg cacagatggt ctttgcatcc tagataaaaa acctcttcat|240|
|gaaataaaac cccaaagcat tgagaatgcc agcgacattg ctttgtactc gggcttgggt|300|
|gctgccgtcg tggccgttgc agtcctggtc attggtgtca cctttacag acggagccag|360|
|agtgactatg cgtggacgt cattgactct tctgcattga caggtggctt ccagaccttc|420|
|aacttcaaaa cagtccgtca aggtaactcc ctgctcctga attctgccat gcagccagat|480|
|ctgacagtga gccggacata cagcggaccc atctgtctgc aggaccctct ggacaaggag|540|
|ctcatgacag agtcctcact ctttaaccct tgtcggaca tcaaagtgaa agtccagagc|600|
|tcgttcatgg tttccctggg agtgtctgag agagctgagt accacggcaa gaatcattcc|660|
|aggacttttc cccatggaaa caaccacagc tttagtacaa tgcatcccag aaataaaatg|720|

-continued

```
ccctacatcc aaaatctgtc atcactcccc acaaggacag aactgaggac aactggtgtc        780
tttggccatt tagggggggcg cttagtaatg ccaaatacag gggtgagctt actcatacca      840
cacggtgcca tcccagagga gaattcttgg gagatttata tgtccatcaa ccaaggtgaa      900
cccagcctcc agtcagatgg ctctgaggtg ctcctgagtc ctgaagtcac ctgtggtcct      960
ccagacatga tcgtcaccac tccctttgca ttgaccatcc cgcactgtgc agatgtcagt    1020
tctgagcatt ggaatatcca tttaaagaag aggacacagc agggcaaatg ggaggaagtg    1080
atgtcagtgg aagatgaatc tacatcctgt tactgccttt tggacccctt tgcgtgtcat    1140
gtgctcctgg acagctttgg gacctatgcg ctcactggag agccaatcac agactgtgcc    1200
gtgaagcaac tgaaggtggc ggttttttggc tgcatgtcct gtaactccct ggattacaac    1260
ttgagagttt actgtgtgga caatacccct tgtgcatttc aggaagtggt ttcagatgaa    1320
aggcatcaag gtggacagct cctggaagaa ccaaaattgc tgcatttcaa agggaatacc    1380
tttagtcttc agatttctgt ccttgatatt cccccattcc tctggagaat taaaccattc    1440
actgcctgcc aggaagtccc gttctcccgc gtgtggtgca gtaaccggca gcccctgcac    1500
tgtgccttct ccctggagcg ttatacgccc actaccaccc agctgtcctg caaaatctgc    1560
attcggcagc tcaaaggcca tgaacagatc ctccaagtgc agacatcaat cctagagagt    1620
gaacgagaaa ccatcacttt cttcgcacaa gaggacagca ctttccctgc acagactggc    1680
cccaaagcct tcaaaattcc ctactccatc agacagcgga tttgtgctac atttgatacc    1740
cccaatgcca aaggcaagga ctggcagatg ttagcacaga aaaacagcat caacaggaat    1800
ttatcttatt tcgctacaca aagtagccca tctgctgtca ttttgaacct gtgggaagct    1860
cgtcatcagc atgatggtga tcttgactcc ctggcctgtg cccttgaaga gattgggagg    1920
acacacacga aactctcaaa catttcagaa tcccagcttg atgaagccga cttcaactac    1980
agcaggcaaa atggactcta g                                              2001
```

<210> SEQ ID NO 30
<211> LENGTH: 666
<212> TYPE: PRT
<213> ORGANISM: homo sapiens

<400> SEQUENCE: 30

```
Met Ala Ala Asn Ile Val Ala Lys Arg Arg Ser Leu Ser Ala Thr Val
  1               5                  10                  15

Val Val Tyr Val Asp Gly Ser Trp Glu Val Trp Ser Glu Trp Ser Val
             20                  25                  30

Cys Ser Pro Glu Cys Glu His Leu Arg Ile Arg Glu Cys Thr Ala Pro
         35                  40                  45

Pro Pro Arg Asn Gly Gly Lys Phe Cys Glu Gly Leu Ser Gln Glu Ser
     50                  55                  60

Glu Asn Cys Thr Asp Gly Leu Cys Ile Leu Asp Lys Lys Pro Leu His
 65                  70                  75                  80

Glu Ile Lys Pro Gln Ser Ile Glu Asn Ala Ser Asp Ile Ala Leu Tyr
                 85                  90                  95

Ser Gly Leu Gly Ala Ala Val Val Ala Val Ala Val Leu Val Ile Gly
            100                 105                 110

Val Thr Leu Tyr Arg Arg Ser Gln Ser Asp Tyr Gly Val Asp Val Ile
        115                 120                 125

Asp Ser Ser Ala Leu Thr Gly Gly Phe Gln Thr Phe Asn Phe Lys Thr
    130                 135                 140
```

-continued

```
Val Arg Gln Gly Asn Ser Leu Leu Asn Ser Ala Met Gln Pro Asp
145                 150                 155                 160

Leu Thr Val Ser Arg Thr Tyr Ser Gly Pro Ile Cys Leu Gln Asp Pro
                165                 170                 175

Leu Asp Lys Glu Leu Met Thr Glu Ser Ser Leu Phe Asn Pro Leu Ser
                180                 185                 190

Asp Ile Lys Val Lys Val Gln Ser Ser Phe Met Val Ser Leu Gly Val
                195                 200                 205

Ser Glu Arg Ala Glu Tyr His Gly Lys Asn His Ser Arg Thr Phe Pro
    210                 215                 220

His Gly Asn Asn His Ser Phe Ser Thr Met His Pro Arg Asn Lys Met
225                 230                 235                 240

Pro Tyr Ile Gln Asn Leu Ser Ser Leu Pro Thr Arg Thr Glu Leu Arg
                245                 250                 255

Thr Thr Gly Val Phe Gly His Leu Gly Gly Arg Leu Val Met Pro Asn
                260                 265                 270

Thr Gly Val Ser Leu Leu Ile Pro His Gly Ala Ile Pro Glu Glu Asn
                275                 280                 285

Ser Trp Glu Ile Tyr Met Ser Ile Asn Gln Gly Glu Pro Ser Leu Gln
                290                 295                 300

Ser Asp Gly Ser Glu Val Leu Leu Ser Pro Glu Val Thr Cys Gly Pro
305                 310                 315                 320

Pro Asp Met Ile Val Thr Thr Pro Phe Ala Leu Thr Ile Pro His Cys
                325                 330                 335

Ala Asp Val Ser Ser Glu His Trp Asn Ile His Leu Lys Lys Arg Thr
                340                 345                 350

Gln Gln Gly Lys Trp Glu Val Met Ser Val Glu Asp Glu Ser Thr
                355                 360                 365

Ser Cys Tyr Cys Leu Leu Asp Pro Phe Ala Cys His Val Leu Leu Asp
    370                 375                 380

Ser Phe Gly Thr Tyr Ala Leu Thr Gly Glu Pro Ile Thr Asp Cys Ala
385                 390                 395                 400

Val Lys Gln Leu Lys Val Ala Val Phe Gly Cys Met Ser Cys Asn Ser
                405                 410                 415

Leu Asp Tyr Asn Leu Arg Val Tyr Cys Val Asp Asn Thr Pro Cys Ala
                420                 425                 430

Phe Gln Glu Val Val Ser Asp Glu Arg His Gln Gly Gly Gln Leu Leu
    435                 440                 445

Glu Glu Pro Lys Leu Leu His Phe Lys Gly Asn Thr Phe Ser Leu Gln
450                 455                 460

Ile Ser Val Leu Asp Ile Pro Pro Phe Leu Trp Arg Ile Lys Pro Phe
465                 470                 475                 480

Thr Ala Cys Gln Glu Val Pro Phe Ser Arg Val Trp Cys Ser Asn Arg
                485                 490                 495

Gln Pro Leu His Cys Ala Phe Ser Leu Glu Arg Tyr Thr Pro Thr Thr
                500                 505                 510

Thr Gln Leu Ser Cys Lys Ile Cys Ile Arg Gln Leu Lys Gly His Glu
                515                 520                 525

Gln Ile Leu Gln Val Gln Thr Ser Ile Leu Glu Ser Glu Arg Glu Thr
                530                 535                 540

Ile Thr Phe Phe Ala Gln Glu Asp Ser Thr Phe Pro Ala Gln Thr Gly
545                 550                 555                 560
```

```
Pro Lys Ala Phe Lys Ile Pro Tyr Ser Ile Arg Gln Arg Ile Cys Ala
            565                 570                 575
Thr Phe Asp Thr Pro Asn Ala Lys Gly Lys Asp Trp Gln Met Leu Ala
            580                 585                 590
Gln Lys Asn Ser Ile Asn Arg Asn Leu Ser Tyr Phe Ala Thr Gln Ser
            595                 600                 605
Ser Pro Ser Ala Val Ile Leu Asn Leu Trp Glu Ala Arg His Gln His
        610                 615                 620
Asp Gly Asp Leu Asp Ser Leu Ala Cys Ala Leu Glu Glu Ile Gly Arg
625                 630                 635                 640
Thr His Thr Lys Leu Ser Asn Ile Ser Glu Ser Gln Leu Asp Glu Ala
            645                 650                 655
Asp Phe Asn Tyr Ser Arg Gln Asn Gly Leu
            660                 665
```

<210> SEQ ID NO 31
<211> LENGTH: 1968
<212> TYPE: DNA
<213> ORGANISM: homo sapiens

<400> SEQUENCE: 31

| | | | | | |
|---|---|---|---|---|---|
| atggcagcca | acatcgtggc | taagaggaga | agcctgtcgg | ccactgttgt | ggtctacgtg | 60 |
| gatgggagct | gggaagtgtg | gagcgaatgg | tccgtctgca | gtccagagtg | tgaacatttg | 120 |
| cggatccggg | agtgcacagc | accaccccg | agaaatgggg | gcaaattctg | tgaaggtcta | 180 |
| agccaggaat | ctgaaaactg | cacagatggt | ctttgcatcc | taggcattga | aaatgccagc | 240 |
| gacattgctt | tgtactcggg | cttgggtgct | gccgtcgtgg | ccgttgcagt | cctggtcatt | 300 |
| ggtgtcaccc | tttacagacg | gagccagagt | gactatggcg | tggacgtcat | tgactcttct | 360 |
| gcattgacag | gtggcttcca | gaccttcaac | ttcaaaacag | tccgtcaagg | taactccctg | 420 |
| ctcctgaatt | ctgccatgca | gccagatctg | acagtgagcc | ggacatacag | cggacccatc | 480 |
| tgtctgcagg | accctctgga | caaggagctc | atgacagagt | cctcactctt | taacccttg | 540 |
| tcggacatca | aagtgaaagt | ccagagctcg | ttcatggttt | ccctgggagt | gtctgagaga | 600 |
| gctgagtacc | acggcaagaa | tcattccagg | acttttcccc | atggaaacaa | ccacagcttt | 660 |
| agtacaatgc | atcccagaaa | taaatgccc | tacatccaaa | atctgtcatc | actccccaca | 720 |
| aggacagaac | tgaggacaac | tggtgtcttt | ggccatttag | gggggcgctt | agtaatgcca | 780 |
| aatacagggg | tgagcttact | cataccacac | ggtgccatcc | cagaggagaa | ttcttgggag | 840 |
| atttatatgt | ccatcaacca | aggtgaaccc | agcctccagt | cagatggctc | tgaggtgctc | 900 |
| ctgagtcctg | aagtcacctg | tggtcctcca | gacatgatcg | tcaccactcc | ctttgcattg | 960 |
| accatcccgc | actgtgcaga | tgtcagttct | gagcattgga | atatccattt | aaagaagagg | 1020 |
| acacagcagg | gcaaatggga | ggaagtgatg | tcagtggaag | atgaatctac | atcctgttac | 1080 |
| tgccttttgg | accccttgc | gtgtcatgtg | ctcctggaca | gctttgggac | ctatgcgctc | 1140 |
| actggagagc | caatcacaga | ctgtgccgtg | aagcaactga | aggtggcggt | ttttggctgc | 1200 |
| atgtcctgta | actccctgga | ttacaacttg | agagtttact | gtgtggacaa | tacccttgt | 1260 |
| gcatttcagg | aagtggtttc | agatgaaagg | catcaaggtg | gacagctcct | ggaagaacca | 1320 |
| aaattgctgc | atttcaaagg | gaatacctt | agtcttcaga | tttctgtcct | tgatattccc | 1380 |
| ccattcctct | ggagaattaa | accattcact | gcctgccagg | aagtcccgtt | ctcccgcgtg | 1440 |
| tggtgcagta | accggcagcc | cctgcactgt | gccttctccc | tggagcgtta | tacgcccact | 1500 |

-continued

```
accacccagc tgtcctgcaa aatctgcatt cggcagctca aaggccatga acagatcctc   1560
caagtgcaga catcaatcct agagagtgaa cgagaaacca tcactttctt cgcacaagag   1620
gacagcactt tccctgcaca gactggcccc aaagccttca aaattcccta ctccatcaga   1680
cagcggattt gtgctacatt tgatacccc aatgccaaag gcaaggactg gcagatgtta   1740
gcacagaaaa acagcatcaa caggaattta tcttatttcg ctacacaaag tagcccatct   1800
gctgtcattt tgaacctgtg ggaagctcgt catcagcatg atggtgatct tgactccctg   1860
gcctgtgccc ttgaagagat tgggaggaca cacacgaaac tctcaaacat ttcagaatcc   1920
cagcttgatg aagccgactt caactacagc aggcaaaatg gactctag              1968
```

<210> SEQ ID NO 32
<211> LENGTH: 655
<212> TYPE: PRT
<213> ORGANISM: homo sapiens

<400> SEQUENCE: 32

```
Met Ala Ala Asn Ile Val Ala Lys Arg Arg Ser Leu Ser Ala Thr Val
 1               5                   10                  15

Val Val Tyr Val Asp Gly Ser Trp Glu Val Trp Ser Glu Trp Ser Val
                20                  25                  30

Cys Ser Pro Glu Cys Glu His Leu Arg Ile Arg Glu Cys Thr Ala Pro
            35                  40                  45

Pro Pro Arg Asn Gly Gly Lys Phe Cys Glu Gly Leu Ser Gln Glu Ser
        50                  55                  60

Glu Asn Cys Thr Asp Gly Leu Cys Ile Leu Gly Ile Glu Asn Ala Ser
65                  70                  75                  80

Asp Ile Ala Leu Tyr Ser Gly Leu Gly Ala Ala Val Val Ala Val Ala
                85                  90                  95

Val Leu Val Ile Gly Val Thr Leu Tyr Arg Arg Ser Gln Ser Asp Tyr
            100                 105                 110

Gly Val Asp Val Ile Asp Ser Ser Ala Leu Thr Gly Gly Phe Gln Thr
        115                 120                 125

Phe Asn Phe Lys Thr Val Arg Gln Gly Asn Ser Leu Leu Asn Ser
    130                 135                 140

Ala Met Gln Pro Asp Leu Thr Val Ser Arg Thr Tyr Ser Gly Pro Ile
145                 150                 155                 160

Cys Leu Gln Asp Pro Leu Asp Lys Glu Leu Met Thr Glu Ser Ser Leu
                165                 170                 175

Phe Asn Pro Leu Ser Asp Ile Lys Val Lys Val Gln Ser Ser Phe Met
            180                 185                 190

Val Ser Leu Gly Val Ser Glu Arg Ala Glu Tyr His Gly Lys Asn His
        195                 200                 205

Ser Arg Thr Phe Pro His Gly Asn Asn His Ser Phe Ser Thr Met His
    210                 215                 220

Pro Arg Asn Lys Met Pro Tyr Ile Gln Asn Leu Ser Ser Leu Pro Thr
225                 230                 235                 240

Arg Thr Glu Leu Arg Thr Thr Gly Val Phe Gly His Leu Gly Gly Arg
                245                 250                 255

Leu Val Met Pro Asn Thr Gly Val Ser Leu Leu Ile Pro His Gly Ala
            260                 265                 270

Ile Pro Glu Glu Asn Ser Trp Glu Ile Tyr Met Ser Ile Asn Gln Gly
        275                 280                 285

Glu Pro Ser Leu Gln Ser Asp Gly Ser Glu Val Leu Leu Ser Pro Glu
```

| | | 290 | | | 295 | | | 300 | | |
|---|---|---|---|---|---|---|---|---|---|---|
Val | Thr | Cys | Gly | Pro | Pro | Asp | Met | Ile | Val | Thr | Thr | Pro | Phe | Ala | Leu
305 | | | | 310 | | | | 315 | | | | | | | 320

Thr Ile Pro His Cys Ala Asp Val Ser Ser Glu His Trp Asn Ile His
              325                        330                        335

Leu Lys Lys Arg Thr Gln Gln Gly Lys Trp Glu Glu Val Met Ser Val
              340                        345                        350

Glu Asp Glu Ser Thr Ser Cys Tyr Cys Leu Leu Asp Pro Phe Ala Cys
              355                        360                        365

His Val Leu Leu Asp Ser Phe Gly Thr Tyr Ala Leu Thr Gly Glu Pro
370                         375                        380

Ile Thr Asp Cys Ala Val Lys Gln Leu Lys Val Ala Val Phe Gly Cys
385                     390                      395                    400

Met Ser Cys Asn Ser Leu Asp Tyr Asn Leu Arg Val Tyr Cys Val Asp
                  405                        410                        415

Asn Thr Pro Cys Ala Phe Gln Glu Val Val Ser Asp Glu Arg His Gln
              420                        425                        430

Gly Gly Gln Leu Leu Glu Glu Pro Lys Leu Leu His Phe Lys Gly Asn
              435                        440                        445

Thr Phe Ser Leu Gln Ile Ser Val Leu Asp Ile Pro Pro Phe Leu Trp
              450                        455                        460

Arg Ile Lys Pro Phe Thr Ala Cys Gln Glu Val Pro Phe Ser Arg Val
465                     470                      475                    480

Trp Cys Ser Asn Arg Gln Pro Leu His Cys Ala Phe Ser Leu Glu Arg
              485                        490                        495

Tyr Thr Pro Thr Thr Thr Gln Leu Ser Cys Lys Ile Cys Ile Arg Gln
              500                        505                        510

Leu Lys Gly His Glu Gln Ile Leu Gln Val Gln Thr Ser Ile Leu Glu
              515                        520                        525

Ser Glu Arg Glu Thr Ile Thr Phe Phe Ala Gln Glu Asp Ser Thr Phe
              530                        535                        540

Pro Ala Gln Thr Gly Pro Lys Ala Phe Lys Ile Pro Tyr Ser Ile Arg
545                     550                      555                    560

Gln Arg Ile Cys Ala Thr Phe Asp Thr Pro Asn Ala Lys Gly Lys Asp
              565                        570                        575

Trp Gln Met Leu Ala Gln Lys Asn Ser Ile Asn Arg Asn Leu Ser Tyr
              580                        585                        590

Phe Ala Thr Gln Ser Ser Pro Ser Ala Val Ile Leu Asn Leu Trp Glu
              595                        600                        605

Ala Arg His Gln His Asp Gly Asp Leu Asp Ser Leu Ala Cys Ala Leu
610                     615                      620

Glu Glu Ile Gly Arg Thr His Thr Lys Leu Ser Asn Ile Ser Glu Ser
625                     630                      635                    640

Gln Leu Asp Glu Ala Asp Phe Asn Tyr Ser Arg Gln Asn Gly Leu
              645                        650                        655

<210> SEQ ID NO 33
<211> LENGTH: 3411
<212> TYPE: DNA
<213> ORGANISM: homo sapiens

<400> SEQUENCE: 33
agtcactctc tgaagactcc atgagaccca ttcgactcgg ggccctgatc accgaccctt    60
tcccgggctc ccggagcgtg aagaagagcc gccctccgga acgcggcgag gagcatgggg   120

-continued

```
agagcggcgg ccaccgcagg cggcggcgga ggggcgcgcc gctggctccc gtggctgggg        180
ctgtgcttct gggcggcagg gaccgcggct gcccgaggaa ctgacaatgg cgaagccctt        240
cccgaatcca tcccatcagc tcctgggaca ctgcctcatt tcatagagga gccagatgat        300
gcttatatta tcaagagcaa ccctattgca ctcaggtgca aagcgaggcc agccatgcag        360
atattcttca aatgcaacgg cgagtgggtc catcagaacg agcacgtctc tgaagagact        420
ctggacgaga gctcaggttt gaaggtccgc gaagtgttca tcaatgttac taggcaacag        480
gtggaggact tccatgggcc cgaggactat tggtgccagt gtgtggcgtg agccacctg         540 ggtacctcca agagcaggaa ggcctctgtg cgcatagcct atttacggaa aaactttgaa        600
caagacccac aaggaaggga agttcccatt gaaggcatga ttgtactgca ctgccgccca        660
ccagagggag tccctgctgc cgaggtggaa tggctgaaaa atgaagagcc cattgactct        720
gaacaagacg agaacattga caccagggct gaccataacc tgatcatcag gcaggcacgg        780
ctctcggact caggaaatta cacctgcatg gcagccaaca tcgtggctaa gaggagaagc        840
ctgtcggcca ctgttgtggt ctacgtggat gggagctggg aagtgtggag cgaatggtcc        900
gtctgcagtc cagagtgtga acatttgcgg atccgggagt gcacagcacc accccccgaga       960 aatgggggca aattctgtga aggtctaagc caggaatctg aaaactgcac agatggtctt       1020
tgcatcctag ataaaaaacc tcttcatgaa ataaaacccc aaagcattga gaatgccagc       1080
gacattgctt tgtactcggg cttgggtgct gccgtcgtgg ccgttgcagt cctggtcatt       1140
ggtgtcaccc tttacagacg gagccagagt gactatggcg tggacgtcat tgactcttct       1200
gcattgacag gtggcttcca gaccttcaac ttcaaaacag tccgtcaagc caagaatatc       1260
atggaactaa tgatacaaga aaaatccttt ggtaactccc tgctcctgaa ttctgccatg       1320
cagccagatc tgacagtgag ccggacatac agcggaccca tctgtctgca ggaccctctg       1380
gacaaggagc tcatgacaga gtcctcactc tttaaccctt gtcggacat caaagtgaaa        1440 gtccagagct cgttcatggt ttccctggga gtgtctgaga gagctgagta ccacggcaag       1500
aatcattcca ggacttttcc ccatggaaac aaccacagct ttagtacaat gcatcccaga       1560
aataaaatgc cctacatcca aaatctgtca tcactcccca caaggacaga actgaggaca       1620
actggtgtct ttggccatttt aggggggcgc ttagtaatgc caaatacagg ggtgagctta      1680
ctcataccac acggtgccat cccagaggag aattcttggg agatttatat gtccatcaac       1740
caaggtgaac ccagcctcca gtcagatggc tctgaggtgc tcctgagtcc tgaagtcacc       1800
tgtggtcctc cagacatgat cgtcaccact cccttgcat tgaccatccc gcactgtgca        1860
gatgtcagtt ctgagcattg gaatatccat ttaaagaaga ggacacagca gggcaaatgg       1920
gaggaagtga tgtcagtgga agatgaatct acatcctgtt actgcctttt ggacccctttt     1980 gcgtgtcatg tgctcctgga cagctttggg acctatgcgc tcactggaga gccaatcaca       2040
gactgtgccg tgaagcaact gaaggtggcg ttttttggct gcatgtcctg taactccctg       2100
gattacaact tgagagttta ctgtgtggac aatacccctt gtgcatttca ggaagtggtt       2160
tcagatgaaa ggcatcaagg tggacagctc ctggaagaac caaaattgct gcatttcaaa       2220
gggaatacct ttagtcttca gatttctgtc cttgatattc ccccattcct ctggagaatt      2280
aaaccattca ctgcctgcca ggaagtcccg ttctcccgcg tgtggtgcag taaccggcag       2340
cccctgcact gtgccttctc cctggagcgt tatacgccca ctaccaccca gctgtcctgc       2400
aaaatctgca ttcggcagct caaaggccat gaacagatcc tccaagtgca gacatcaatc       2460
```

-continued

```
ctagagagtg aacgagaaac catcactttc ttcgcacaag aggacagcac tttccctgca    2520
cagactggcc ccaaagcctt caaaattccc tactccatca gacagcggat ttgtgctaca    2580
tttgataccc ccaatgccaa aggcaaggac tggcagatgt tagcacagaa aaacagcatc    2640
aacaggaatt tatcttattt cgctacacaa agtagcccat ctgctgtcat tttgaacctg    2700
tgggaagctc gtcatcagca tgatggtgat cttgactccc tggcctgtgc ccttgaagag    2760
attgggagga cacacacgaa actctcaaac atttcagaat cccagcttga tgaagccgac    2820
ttcaactaca gcaggcaaaa tggactctag tccacttcct cccatgagac agagtgatgg    2880
ccagcttggg gacatttgct ttaaatggga aagaggccgc tttctgccca gtggcgttgg    2940
gggaattcag ccttcattta taatcagtga gattcccctg ttgaagaaac taaattttat    3000
ataggtaaaa catgttaata gggaagagta caagctctct tacatataag agggctctac    3060
tatctccttg gaatccacat ttgggttaac tcctcagatt tggagtggca aggataaaag    3120
tgagggcaga agtagctgtg ggaaaagatg agctatgata atgctgggaa ggcagagatt    3180
gattaagtgc atgctttgaa ataggttttt aatgatgtgc cccaaagggc cagctgattc    3240
tggtactaga ttgtcagagt tttctaccaa ctggcatctg tgatgtcaga gatcattgta    3300
aaaatggctt ttagacgtga aacaaggttg ccaacccatt tgtatgactt caacaacgtc    3360
aaggagggca tttagaattt agaatctgag cacatcacac cagcaccagc t             3411
```